(12) United States Patent
Otsubo et al.

(10) Patent No.: US 7,547,299 B2
(45) Date of Patent: Jun. 16, 2009

(54) DISPOSABLE WEARING ARTICLE

(75) Inventors: Toshifumi Otsubo, Kagawa-ken (JP); Tomoko Sugita, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/920,310

(22) Filed: Aug. 18, 2004

(65) Prior Publication Data

US 2005/0043701 A1    Feb. 24, 2005

(30) Foreign Application Priority Data

Aug. 19, 2003   (JP)   ............... 2003-207945
Jul. 28, 2004   (JP)   ............... 2004-219916

(51) Int. Cl.
*A61F 13/15*   (2006.01)
*A61F 13/20*   (2006.01)

(52) U.S. Cl. ............... 604/387; 604/386; 604/385.03

(58) Field of Classification Search ......... 604/386–391, 604/358, 385.01, 385.22–385.24, 385.27
See application file for complete search history.

(56) References Cited

U.S. PATENT DOCUMENTS 5,624,428 A * 4/1997 Sauer .................. 604/391
5,669,897 A * 9/1997 Lavon et al. .......... 604/385.24
5,926,926 A * 7/1999 Kato .................... 24/442
6,007,527 A * 12/1999 Kawaguchi et al. ...... 604/386
2003/0100880 A1* 5/2003 Magee et al. ........... 604/389

FOREIGN PATENT DOCUMENTS

JP     4-89050    3/1992
JP     6-55623    6/1994

* cited by examiner

*Primary Examiner*—Michele Kidwell
(74) *Attorney, Agent, or Firm*—Lowe Hauptman Ham & Berner, LLP

(57) ABSTRACT

A disposable wearing article has front and rear waist regions, a crotch region extending between these waist regions and a pair of engagement members respectively to inner surfaces of transversely opposite side edge portions of the rear waist region. In the article, each of the engagement members has a fixed portion permanently bonded to the associated side portion of the rear waist region and a first free portion extending inward from the fixed portion in a transverse direction of the rear waist region wherein the first free portion is formed on its inner surface with a fastening means so that the side edge portions of the rear waist region may be releasably engaged with inner or outer surface of the front waist region by means of the engagement members.

13 Claims, 23 Drawing Sheets

DISPOSABLE WEARING ARTICLE

RELATED APPLICATIONS

The present application is based on, and claims priorities from, Japanese Application Serial Number 2003-207945, filed Aug. 19, 2003 and Japanese Application Serial Number 2004-219916, filed Jul. 28, 2004, the disclosures of which are hereby incorporated by reference herein in its entirety.

BACKGROUND OF THE INVENTION

The present invention relates to a disposable wearing article used to absorb and then to retain bodily waste discharged thereon.

There has already been disclosed a disposable diaper having front and rear waist regions, a crotch region extending between these two waist regions, and pressure sensitive adhesive double coated tape strips extending in a transverse direction and attached to transversely opposite side edge portions in the front and rear waist regions so that the side edge portions of the front waist region and the side edge portions of the rear waist region may be put flat and connected together by means of these pressure sensitive adhesive double coated tape strips (See Japanese Unexamined Patent Application Publication No. 1992-89050, hereinafter referred to as "Citation 1"). A waist-hole and a par of leg-holes are formed as the front and rear waist regions are connected with each other in such manner. Parent or care personnel may put the article on the wearer s body by guiding legs of the wearer through the waist-hole, then through the leg-holes and drawing the article upward along the wearer's waist.

In addition, there has already been disclosed a disposable wearing article having front and rear waist regions, a crotch region extending between these two waist regions, and engagement members extending in a transverse direction and attached to transversely opposite side edge portions in the front and rear waist regions so that the side edge portions of the front waist region and the side edge portions of the rear waist region may be connected together by means of these engagement members (See Japanese Unexamined Utility Model Application Publication No. 1994-55623, hereinafter referred to as "Citation 2"). One of the engagement members is defined by hooks constituting the so-called mechanical fastener and attached to the outer surface of the front waist region along the transversely opposite side edge portions thereof. The other of the engagement members is defined by loops constituting the mechanical fastener and attached to the inner surface of the rear waist region along the transversely opposite side edge portions thereof. Parent or care personnel may put the article disclosed in Citation 2 on the wearer's body in a manner as follows: along the respective transversely opposite side edges portions of the front and rear waist regions, the inner surface of the rear waist region is placed upon the outer surface of the front waist region; the hooks and the loops are put in mutual engagement to connect the front and rear waist regions with each other whereupon a waist-hole and a pair of leg-holes are formed; then the wearer's legs are guided through the waist-hole, then through the leg-holes; and finally the article is drawn upward along the wearer's waist.

After the article disclosed in Citation 1 has been put on the wearer's body with the front and rear waist regions connected together by means of the pressure sensitive adhesive double coated tape strips, a peel force intending to release these double coated tape strips from one another is exerted upon the transversely opposite side edges of the front and rear waist regions as these side edge portions of the front and rear waist regions are pulled by the wearer's waist in a waist surrounding direction. If an adhesive force between the pressure sensitive adhesive double coated tape strips is relatively low, it will be apprehended that the peel force exerted upon the side edge portions of the front and rear waist regions might readily release these adhesive double coated tape strips from one another and thereby the front and rear waist regions might be unintentionally disconnected from each other as the transversely opposite side edge portions of the front and rear waist regions are pulled by the wearer's waist in a waist surrounding direction.

After the article disclosed in Citation 1 has been put on the wearer's body with the front and rear waist regions connected together by means of those engagement members, the hooks and the loops are further tightly engaged one with another as the front and rear waist regions are pulled by the wearer's waist in a waist surrounding direction. Depending on a degree of the pulling force, there is anxiety that the hooks and the loops might be too tightly engaged with one another to be easily disengaged from one another for disposal of the article after the article has been soiled with body waste.

SUMMARY OF THE INVENTION

In view of the problem as has been described above, it is an object of the present invention to provide a disposable wearing article improved so as to eliminate a possibility that the front and rear waist regions might be unintentionally disconnected from each other during use of the article and to ensure that the side edge portions of the front and rear waist regions can be easily separated from each other.

The object set forth above is achieved, according to the present invention, by an improvement in the disposable wearing article having front and rear waist regions, a crotch region extending between these waist regions and a pair of engagement members respectively to inner surfaces of transversely opposite side edge portions of one of the front and rear waist region so that the side edge portions of these waist regions are releasably engaged with inner or outer surface of these waist region by means of the engagement members.

The improvement according to the present invention is in that the engagement members respectively have fixed portions permanently bonded to the side edge portions of the waist region and a first free portions extending inward from the fixed portions in a transverse direction and the first free portions are formed on respective inner surfaces with a fastening means.

According to one preferred embodiment of the invention, the fastening means is one of hooks of a mechanical fastener and adhesive of an adhesive fastener and provided on the inner surface of the first free portion.

According to another preferred embodiment of the invention, the engagement members respectively include second free portions lying on the side opposed to the first free portions with respective the fixed portions therebetween and extending outward from the respective fixed portions in the transverse direction and the one of the hooks and adhesive are formed on respective inner surfaces of the second free portions.

According to still another preferred embodiment of the invention, the engagement members respectively have a length dimension measured in the longitudinal direction approximately same as the corresponding dimension of the side edge portions of the waist region.

According to further another preferred embodiment of the invention, the side edge portions of the front and rear waist regions are stretchable at least in the transverse direction of the longitudinal and transverse directions.

In the disposable wearing article according to the present invention, even when a force tending to disconnect the side edge portions of the front and rear waist regions from one another is exerted on these side edge portions of the article put on the wearer's body with the engagement members engaged with the inner surface of the front or rear waist region, such pulling force functions as the shearing force exerted on the side edge portions of the waist region and the engagement members. Therefore, the free portions of the engagement members are not easily disengaged from the inner surface of the waist region and it is not apprehended that the front and rear waist regions might be unintentionally disconnected from each other during use of the article. Regardless of the particular wearer's waist size, the article can be appropriately tightened around the wearer's waist and such adjustment makes it possible to prevent the article from slipping down during use of the article because this article allows a fitness of the article around the wearer's waist to be adjusted. The used article can be maintained in its folded state by the engagement members for disposal.

In the case of the article wherein the fixed portions of the engagement members also are provided on the respective inner surfaces with the fastening means, even if the force exerted on the side edge portions of the front and rear waist regions tends to separate these side edge portions from one another, such force functions as a shearing force exerted on the side edge portions of the waist region and the engagement members whether the article 1B is put on the wearer's body by engaging the fixed portions as well as the free portions of the engagement member with the inner surface of the waist region or by the fixed portions as well as the free portions of the engagement members with the outer surface of the waist region. Thus the fixed portions as well as the free portions of the engagement members are not easily peeled off from the inner or outer surface of the waist region and there is no anxiety that the front and rear waist regions might be unintentionally disconnected from each other during use of the article.

In the case of the diaper wherein the engagement members have, in addition to the fixed portions and the first free portions the second free portions of which the respective inner surfaces formed with the fastening means, these second free portions are engaged with the inner or outer surface of the waist region so as to enhance engagement between the waist region and the engagement members. In this article, the second free portions of the engagement members are engaged with the outer surfaces of the respective side edge portions of the waist region by means of the hooks so that, even if any peeling force is exerted on the fixed portions, such peeling force is restricted by the second free portions and it is not apprehended that the peeling force might be significantly exerted on the fixed portions.

In the article wherein the length dimension of the engagement member measured in the longitudinal direction is approximately same as the corresponding dimension of the side edge of the waist region, the side edge portions of the one waist region can be engaged with the side edge portions of the other waist region substantially over the full length dimension of these side edge portions. In this way, the front and rear waist regions can be reliably connected with each other.

DETAILED DESCRIPTION OF THE PREFERRED EMBODIMENTS

Details of a disposable wearing article according to the present invention will be more fully understood from the description given hereunder with reference to the accompanying drawings.

Figure 1:
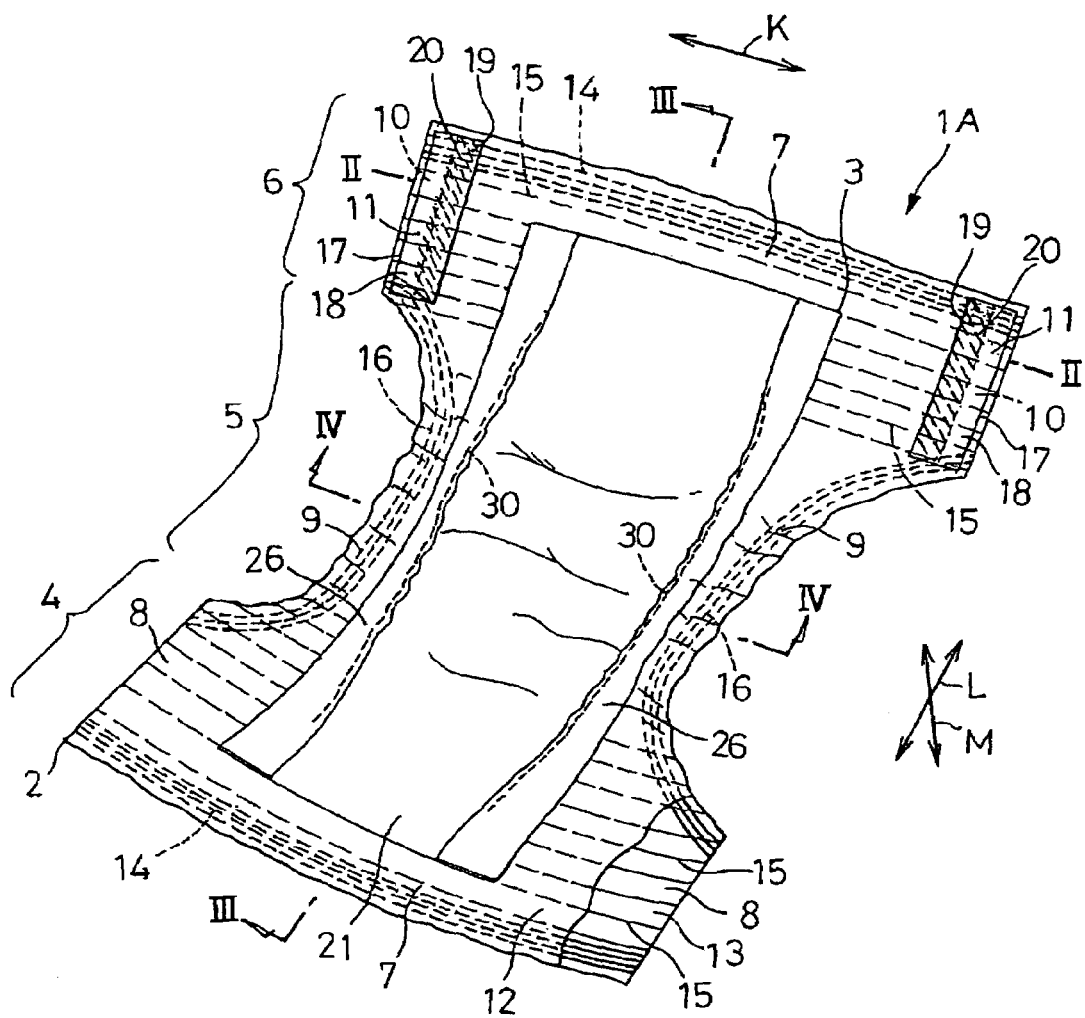
FIG. 1 is a partially cutaway perspective view showing a typical embodiment of the disposable wearing article.
Figure 2:
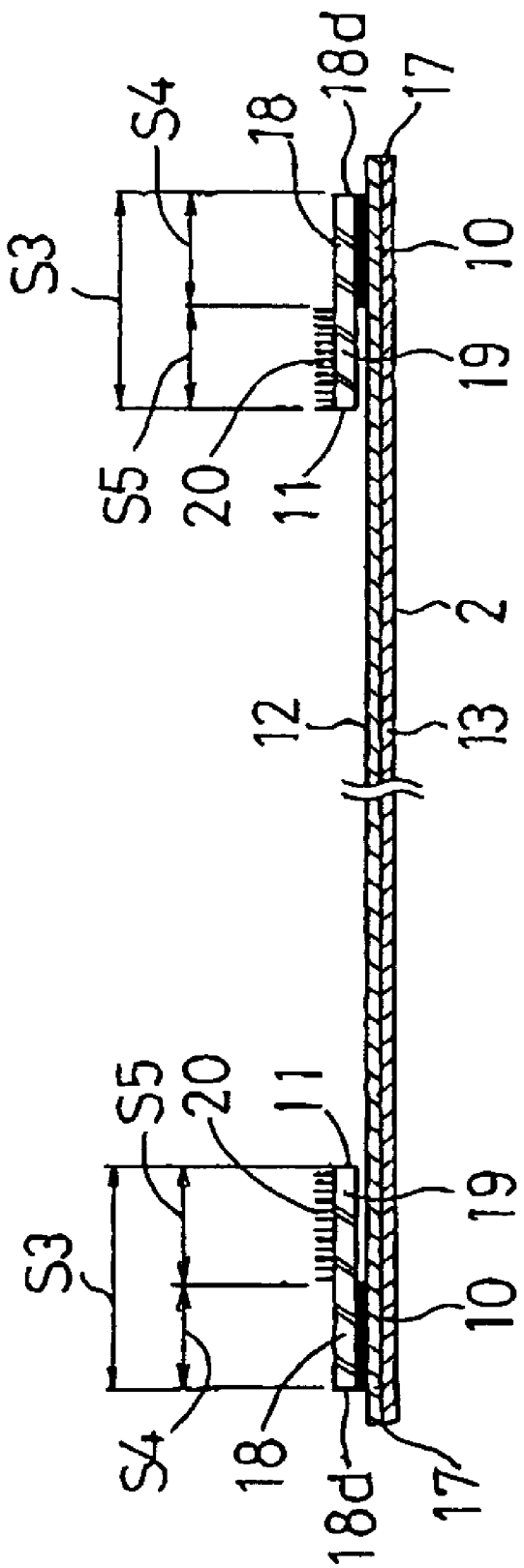
FIG. 2 is a sectional view taken along the line II-II in FIG. 1.
Figure 3:
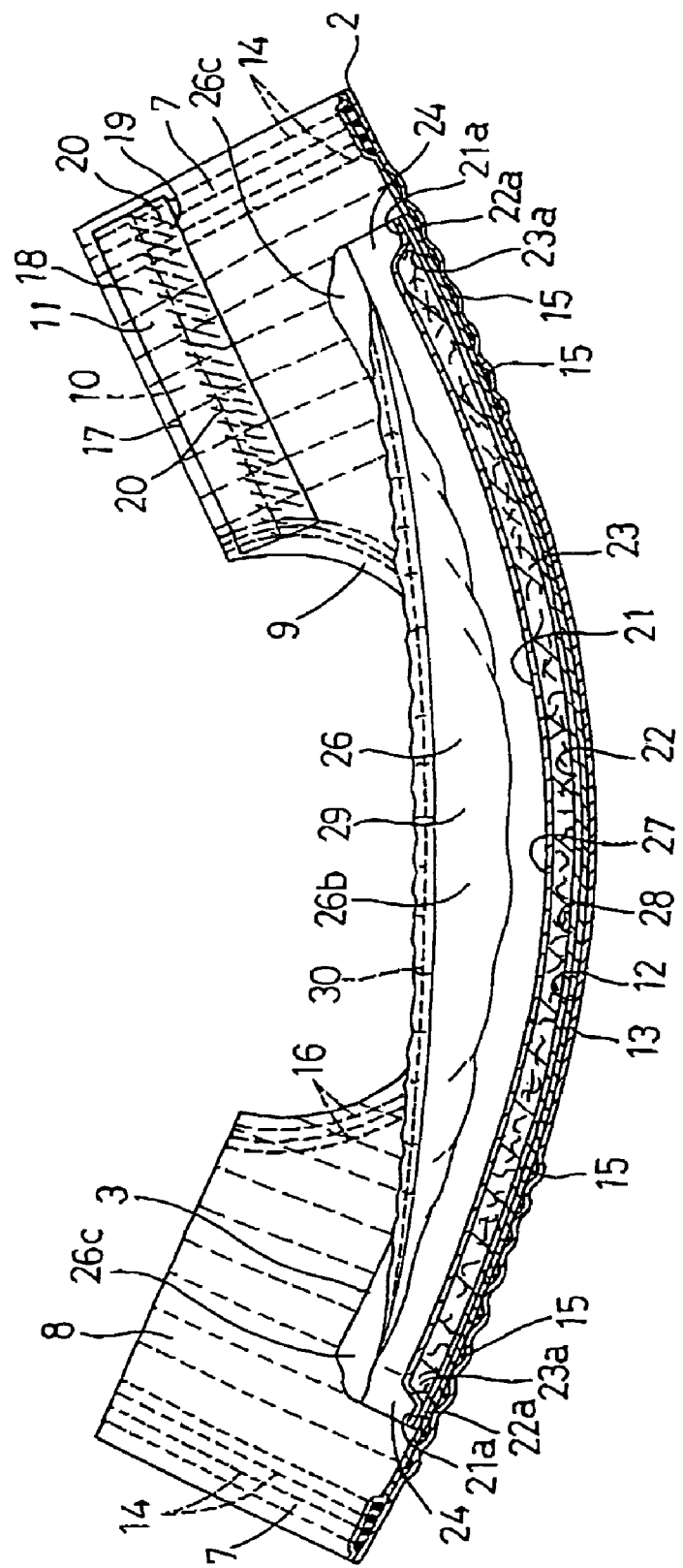
FIG. 3 is a sectional view taken along the line III-III in FIG. 1.
Figure 4:
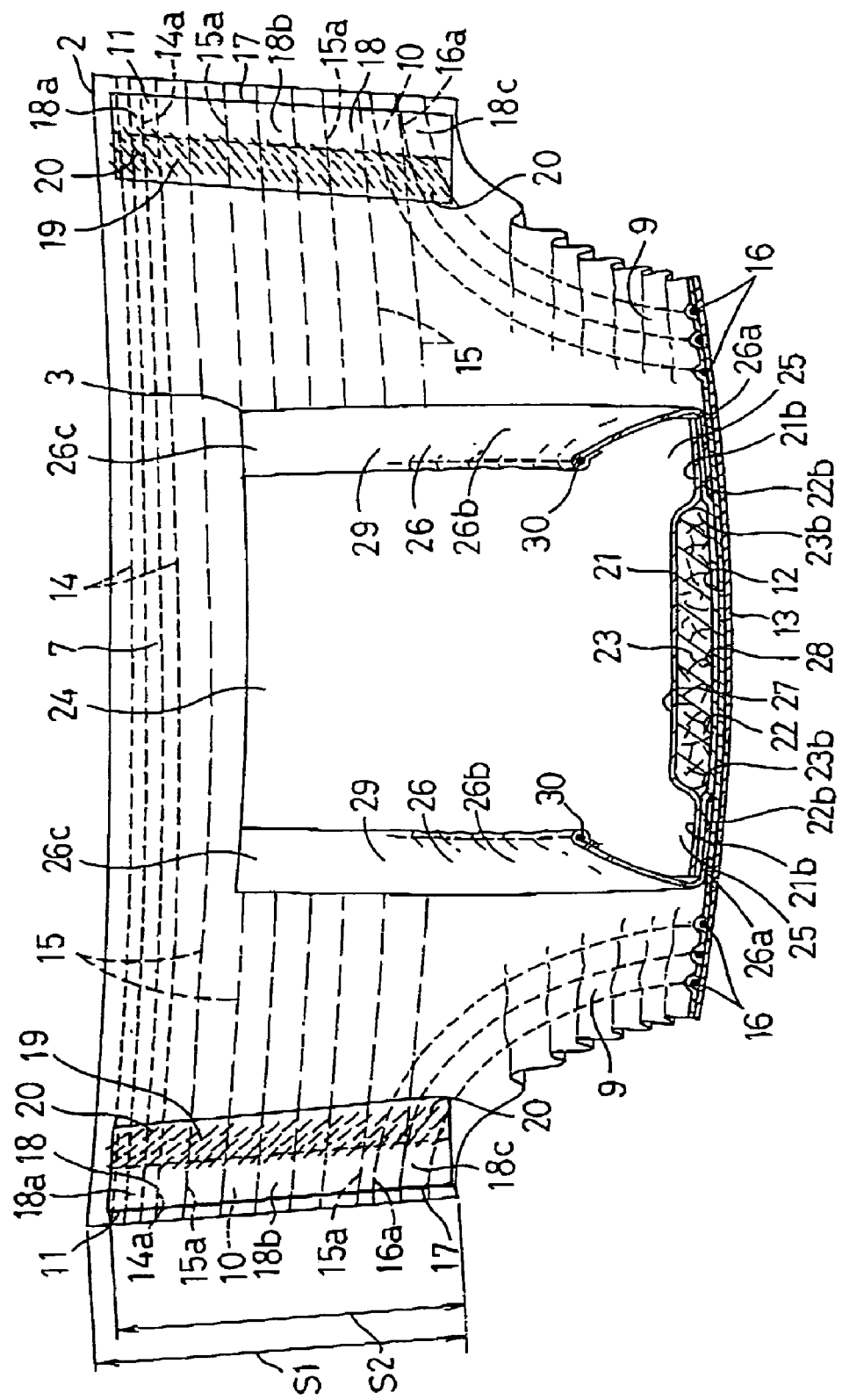
FIG. 4 is a sectional view taken along the line IV-IV in FIG. 1.

FIG. 1 is a perspective view showing a disposable wearing article 1A according to a typical embodiment of the invention as partially broken away, FIG. 2 is a sectional view taken along a line II-II in FIG. 1, FIG. 3 is a sectional view taken along a line III-III in FIG. 1 and FIG. 4 is a sectional view taken along a line IV-IV in FIG. 1. In FIG. 1, a transverse direction is indicated by an arrow K, a longitudinal direction is indicated by an arrow L and a thickness direction is indicated by an arrow M. As used herein, "inner surfaces" of an outer sheet 2, engagement members 11 and top- and back-sheets 21, 22 refer to the surfaces thereof facing the wearer's skin and "outer surfaces" thereof refer to the surfaces thereof facing away from the wearer's skin.

The article 1A comprises a liquid-impervious outer sheet 2 defining an outer shape of the article 1A and a laminated panel 3 attached to the inner surface of the outer sheet 2. The article 1A defines, in a longitudinal direction, a front waist region 4, a rear waist region 6, a crotch region 5 extending between these waist regions 4, 6, longitudinally opposite end portions 7 extending across the front and rear waist regions 4, 6 in a transverse direction, and transversely opposite side edge portions 8, 9, 10 extending in the front waist region 4, the crotch region 5 and the rear waist region 6 in a longitudinal direction. The side edge portions 8 of the front waist region 4 have a substantially same length dimension as a length dimension of the side edge portions 10 of the rear waist region 6. Engagement members 11 are attached to the side edge portions 10 of the rear waist region 6.

The outer sheet 2 defines the front and rear waist regions 4, 6, the crotch region 5, the longitudinally opposite end portions and the transversely opposite side edge portions 8, 9, 10. The outer sheet 2 is formed by composite nonwoven fabric consisting of a pair of non-stretchable hydrophobic fibrous nonwoven fabric layers 12, 13 placed upon and bonded to each other. Mutually opposed surfaces of these nonwoven fabric layers 12, 13 are intermittently bonded to each other by means of adhesive (not shown). The outer sheet 2 curves inward along the side edge portions extending in the crotch region 5 so as to describe circular arcs which are convex it the transverse direction of the article 1A. Thus, the outer sheet 2 presents a substantially hourglass-like planar shape. A plurality of first and second waist-surrounding elastic members 14, 15 and a plurality of leg-surrounding elastic members 16 are contractibly attached to the outer sheet 2 so that the outer sheet 2 may be formed with a plurality of gathers as these elastic members 14, 15, 16 contract.

The first waist-surrounding elastic members 14 extend along the longitudinally opposite end portions 7 in the transverse direction. The first waist-surrounding elastic members 14 comprise a plurality of elastic strands arranged substantially at regular intervals in the longitudinal direction. The second waist-surrounding members 15 are laid between the first waist-surrounding elastic members 14 and the leg-surrounding elastic members 16 and extend across the front and rear waist regions 4, 6 in the transverse direction. The second waist-surrounding elastic members 15 comprise a plurality of elastic strands arranged substantially at regular intervals in the longitudinal direction. The leg-surrounding elastic members 16 comprise a plurality of elastic strands extending along the side edges 8, 9, 10 in the longitudinal direction from the crotch region 5 toward the front and rear waist regions 4, 6. These elastic member 14, 15, 16 are interposed between the nonwoven fabric layers 12, 13 constituting the outer sheet 2 and intermittently bonded to the mutual opposed surfaces of these nonwoven fabric layers 12, 13. Specifically, these elastic members 14, 15, 16 are bonded to these nonwoven fabric layers 15, 16 while these elastic members 14, 15, 16 are stretched at a predetermined ratio. The presence of these first and second waist-surrounding elastic members 14, 15 makes the respective side edge portions 8, 10 of the front and rear waist regions 4, 6 elastically stretchable in the transverse direction.

The engagement members 11 are laid on the inner surface of the rear waist region 6 along the side edge portions 10 thereof and extend in the longitudinal direction. Each of the engagement members 11 is provided in a rectangular shape which is relatively long in the longitudinal direction and its length dimension S2 measured in the longitudinal direction is substantially same as a length dimension S1 of the side edge portion 10 measured in the longitudinal direction (See FIG. 4). The engagement member 11 has a fixed portion 18 permanently bonded to the side edge portion 10 in the vicinity of its outermost edge 17 and extending in the longitudinal direction and a free portion 19 extending in parallel to and inward from the fixed portion 18 in the transverse direction of the rear waist region 6.

The fixed portion 18 has its outer surface permanently bonded to the inner surface of the outer sheet 2 (i.e., the nonwoven fabric layer 12). Of the fixed portion 18, an upper zone 18a is placed upon transversely opposite end portions 14a of the first waist-surrounding elastic members 14 on the associated side, an intermediate zone 18b is placed upon transversely opposite end portions 15a of the second waist-surrounding elastic members 15 on the associated side and a lower zone 18c is placed upon longitudinally opposite end portions 16a of the leg-surrounding elastic members 16 on the associated side (See FIG. 4). The free portion 19 is not permanently bonded to the outer sheet 2. As can be seen in FIG. 2, the free portion 19 extends in cantilever fashion from the fixed portion 18 and is spaced from the outer sheet 2 by an air gap. The free portion 19 is provided on its whole inner surface with a plurality of hooks 20 constituting the known mechanical fastener. These hooks 20 extend from the inner surface of the free portion 19 in the thickness direction of the article 1A. It should be noted here that these hooks 20 may be replaced by adhesive of the adhesive fastener known in the art.

A length dimension S4 of the fixed portion 18 measured in the transverse direction is approximately a half of a full length dimension S3 of the engagement member 11 measured in the transverse direction and a length dimensions S5 of the free portion 19 measured in the transverse direction is approximately a half of the full length dimension S3 (See FIG. 2). The outermost edge 18d of the fixed portion 18 is placed aside inward from the outermost edge 17 of the side edge portion 10 in order to avoid an anxiety that the outermost edge 18d of the fixed portion 18 might contact the wearer's skin and thereby uncomfortably irritate the wearer's skin.

The panel 3 comprises a liquid-pervious topsheet 21 facing the wearer's skin, a liquid-impervious backsheet 22 facing away from the wearer's skin and a liquid-absorbent core 23 interposed between these top- and backsheets 21, 22. The panel 3 serves to absorb and to retain body waste discharged by the wearer of the article 1A. The panel 3 has a substantially rectangular planar shape and extends between the front and rear waist regions 4, 6. The panel 3 has longitudinally opposite ends 24 extending in the transverse direction and transversely opposite side edges 25 extending in the longitudinal direction between the front and rear waist regions 4, 6. In the panel 3, the outer surface of the backsheet 22 is permanently bonded to the inner surface of the outer sheet 2 (i.e., the nonwoven fabric layer 12) in intermittent or continuous manner. The transversely opposite side edges 25 of the panel 3 are respectively provided with a pair of liquid-resistant leak-barrier sheets 26 extending in the longitudinal direction between the front and rear waist regions 4, 6.

The topsheet 21 is formed by hydrophilic fibrous nonwoven fabric 27 and the backsheet 22 is formed by hydrophobic fibrous nonwoven fabric 28. The core 23 is permanently bonded to at least one of the top- and backsheets 21, 22. The core 23 comprises a mixture of particulate or fibrous super-absorbent polymer and fluff pulp or a mixture of particulate or fibrous super-absorbent polymer, fluff pulp and thermoplastic synthetic resin fiber, in any case, compressed to a given thickness. Preferably, the core 23 is entirely wrapped with liquid-pervious sheet such as tissue paper or hydrophilic fibrous nonwoven fabric in order to prevent the core 23 from getting out of its initial shape and/or to prevent polymer from falling off. The polymer may be starch-based polymer, cellulose-based polymer or synthetic polymer.

The longitudinally opposite end portions 24 are formed by longitudinally opposite end portions 23a, 22a of the top- and backsheets 21, 22, respectively, extending outward in the longitudinal direction beyond the longitudinally opposite ends 23a of the core 23. In these end portions 24, the end portions 21a, 22a of the top- and backsheets 21, 22 are put flat and permanently bonded together. The transversely opposite side edge portions 25 are formed by transversely opposite side edge portions 21b, 22b of the top- and backsheets 21, 22, respectively, extending outward in the transverse direction beyond the transversely opposite side edges 23b of the core 23. In these side edge portions 25, the side edge portions 21b, 22b of the top- and backsheets 21, 22 are put flat and permanently bonded together.

The leak-barrier sheets 26 are formed by hydrophobic fibrous nonwoven fabric 29. Each of these leak-barrier sheets 26 has a fixed lateral portion 26a extending in parallel to the associated side edge 25 of the panel 3 in the longitudinal direction, a movable portion 26b extending in parallel to the fixed lateral portion 26a in the longitudinal direction, and longitudinally opposite fixed end portions 26c of the movable portion 26b. The fixed lateral portion 26a is interposed between the outer sheet 2 and the backsheet 22 and permanently bonded to the inner surface of the outer sheet 2 (i.e., the nonwoven fabric layer 12) and the outer surface of the backsheet 22. A stretchable elastic member 30 extending in the longitudinal direction is contractibly attached to the movable portion 26b in the vicinity of its upper edge. The elastic member 30 is strand-like and permanently bonded to the movable portion 26b so that the elastic member 30 may be wrapped with a part of the movable portion 26b. The longitudinally opposite fixed end portions 26c lying on the respective end portions 25 of the panel 3 are collapsed inward as viewed in the transverse direction and permanently bonded in such state to the outer surface of the topsheet 21. The elastic member 30 contracts as the article 1A curves in the longitudinal direction with the panel 3 inside. In response to this, the movable portion 26b of the leak-barrier sheet 26 rises above the topsheet 21 and forms a barrier against body waste.

Figure 5:
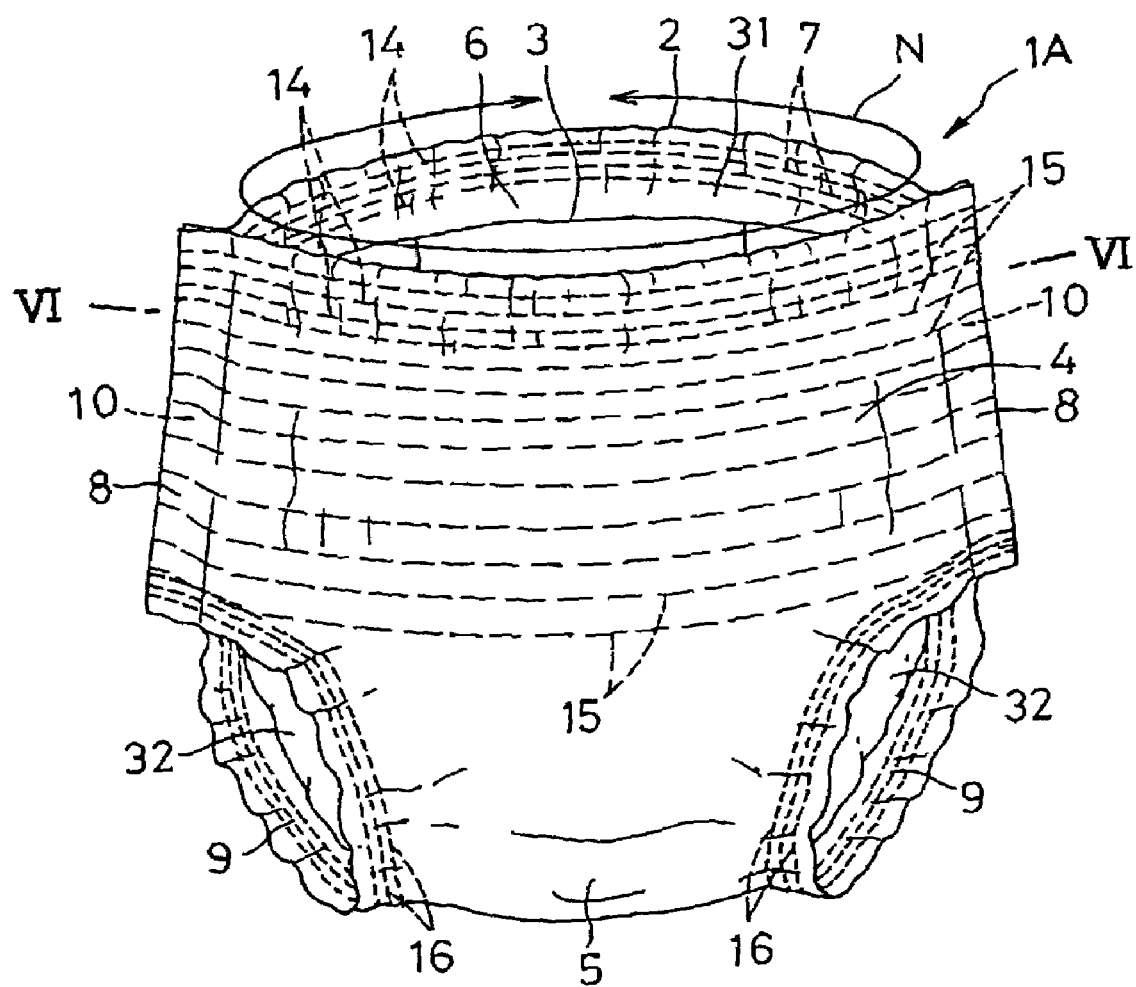
FIG. 5 is a perspective view showing the article of FIG. 1 as put on the wearer's body in one manner of wearing.
Figure 6:
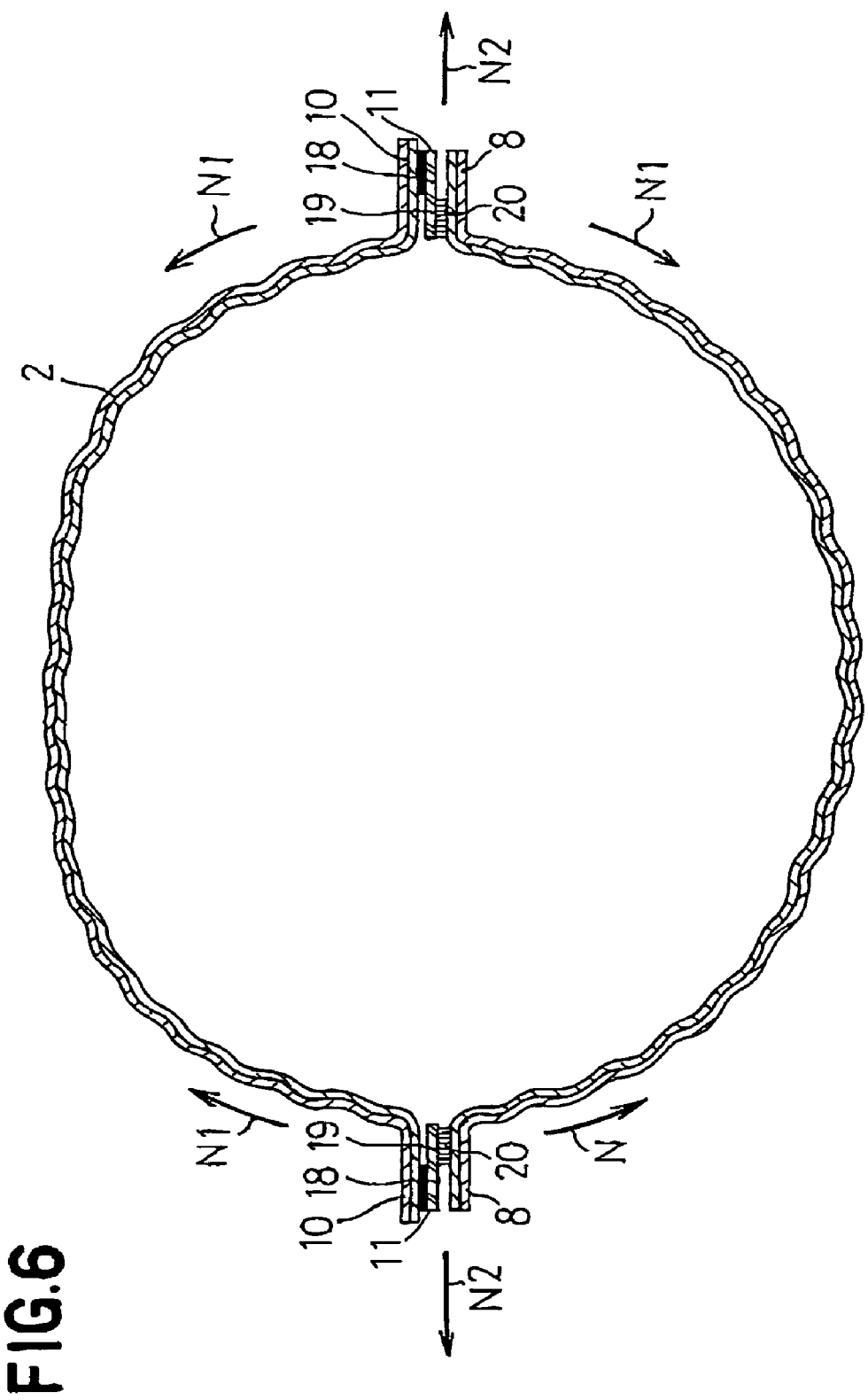
FIG. 6 is a sectional view taken along the line VI-VI in FIG. 5.
Figure 7:
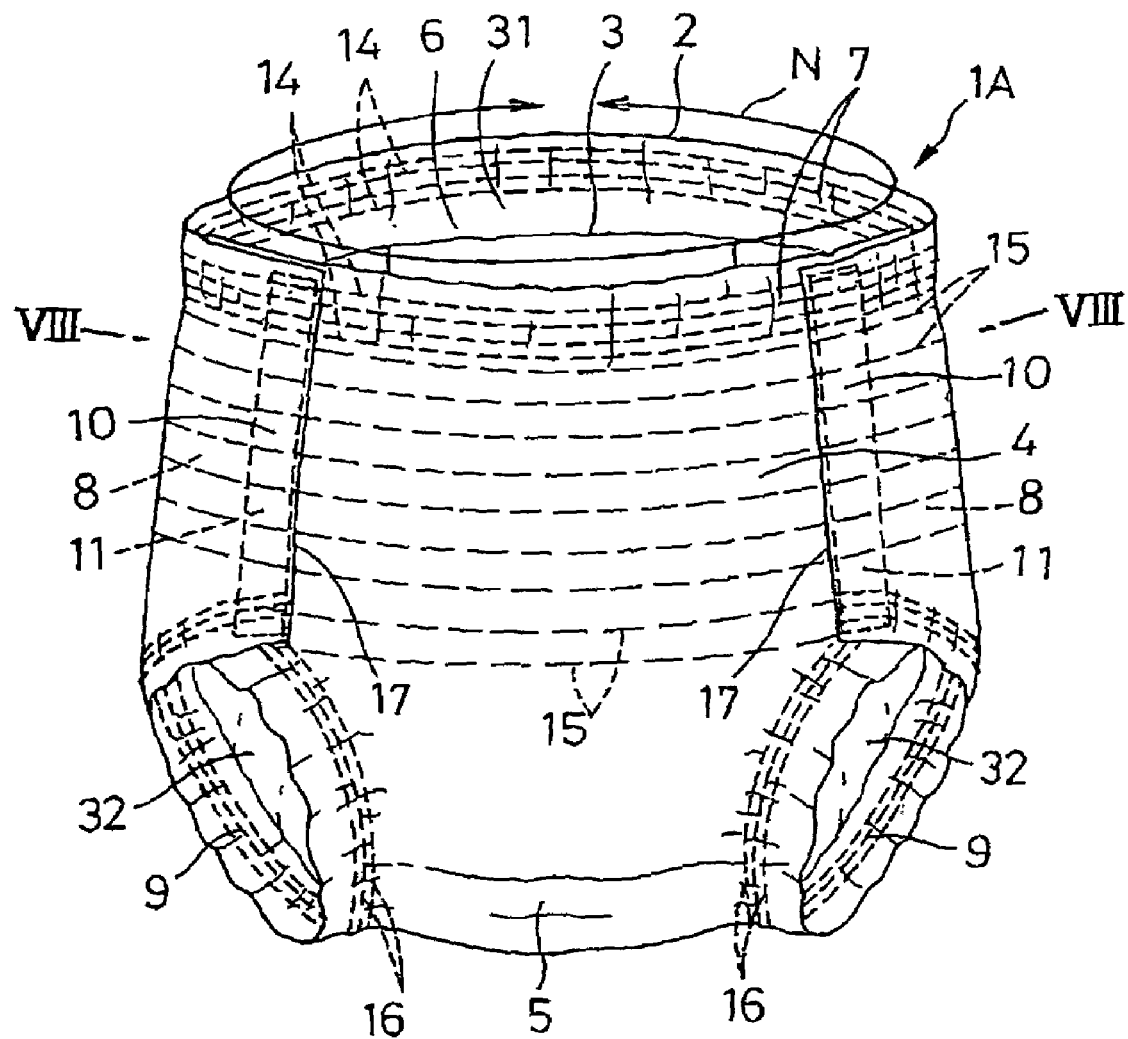
FIG. 7 is a perspective view showing the article of FIG. 1 as put on the wearer's body in another manner of wearing.
Figure 8:
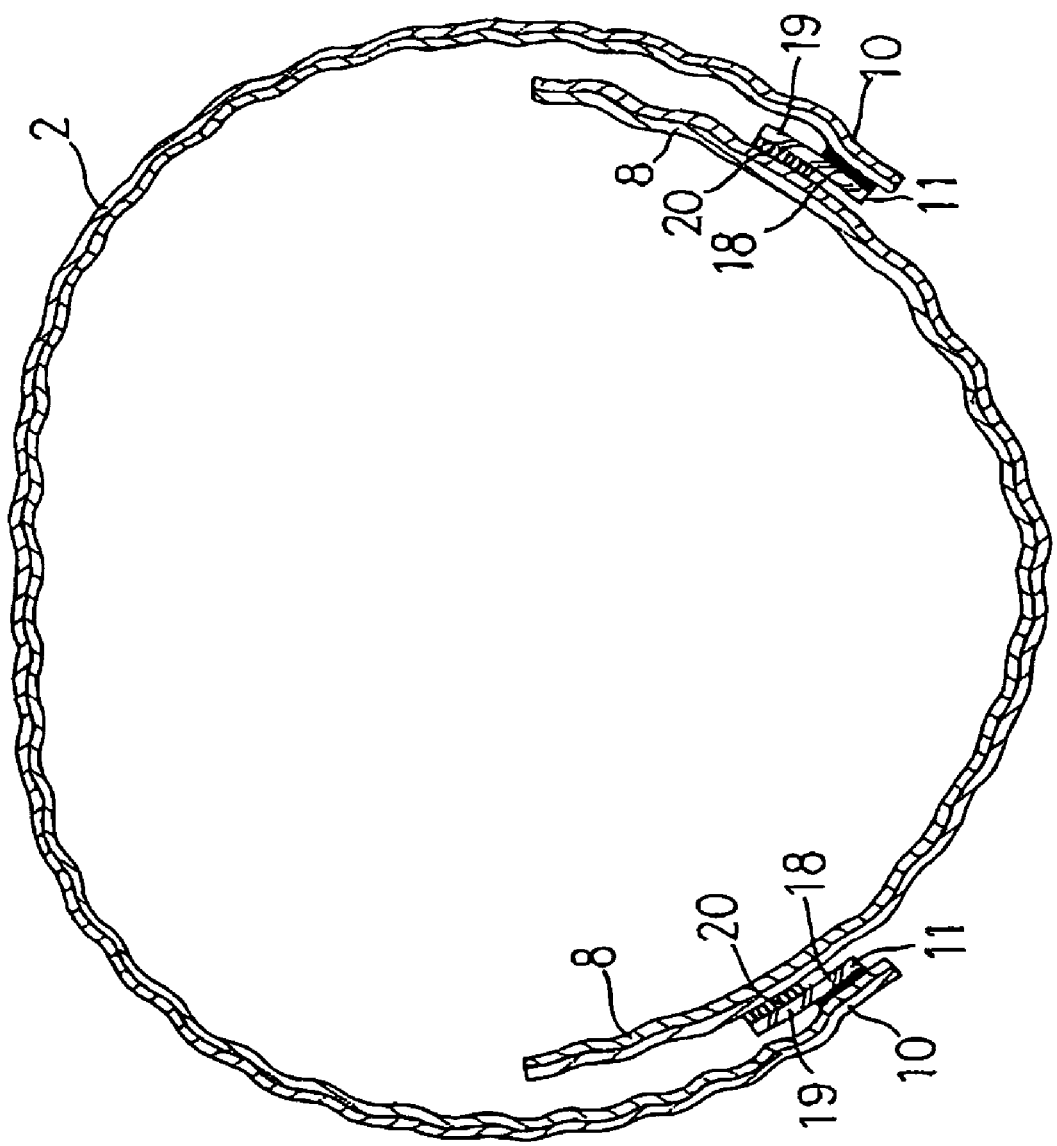
FIG. 8 is a sectional view taken along the line VIII-VIII in FIG. 7.

FIG. 5 is a perspective view showing the article 1A of FIG. 1 as put on the wearer's body in one manner of wearing, FIG. 6 is a sectional view taken along a line VI-VI in FIG. 5, FIG. 7 is a perspective view showing the article 1A of FIG. 1 as put on the wearer's body in another manner of wearing and FIG. 8 is a sectional view taken along a line VIII-VIII in FIG. 7. In FIGS. 5 and 7, a waist-surrounding direction is indicated by an arrow N.

A first sequence followed by parent or care personnel to put the article 1A on the wearer's body comprises steps of placing the inner surface of the rear waist region 6 upon the inner surface of the front waist region 4 along the side edge portions 10, 8 thereof and pressing the engagement members 11 against the side edge portions 8 of the front,waist region 4. By pressing the engagement members 11 against the inner surface of the side edge portions 8, the hooks 20 are caught by individual fibers of the nonwoven fabric layer 12 constituting the outer sheet 2 and thereby the free portions 19 of the engagement members 11 are engaged with the inner surface of the side edge portions 8 of the front waist region 4. In this way, the front and rear waist regions 4, 6 are connected with each other along the side edge portions 8, 10 thereof (See FIG. 5) whereupon the article 1A is formed with a waist-hole 31 and a pair of leg-holes 32. After the front and rear waist regions 4, 6 have been connected with each other, parent or care personnel guides the wearer's legs through the waist-hole 31, then through the leg-holes 32 and draws the article 1A upward along the wearer's waist.

Referring to FIG. 6, the side edge portions 8, 10 of the front and rear waist regions 4, 6 are pulled in the waist surrounding direction indicated by an arrow N1 as the article 1A is put on the wearer's body. Although such pulling force certainly tends to disconnect the side edge portions 8, 10 of the front and rear waist regions 4, 6 from each other, it functions not as a peeling force tending to disengage the engagement members from the side edge portions 8 of the front waist region 4 but as a shearing force indicated by an arrow N2. The hooks 20 are not easily disengaged from the inner surface of the outer sheet 2 merely by such shearing force. In this way, it is not apprehended that the front and rear waist regions 4, 6 might be unintentionally disconnected from each other during use of the article 1A.

A second sequence followed by parent or care personnel to put the article 1A on the wearer's body is distinguished from the first sequence as has been described above in that the second sequence includes additional steps for adjustment. If it has been found that a fitness of the front and rear waist regions 4, 6 around the wearer's waist is insufficient after the article 1A was put on the wearer's body in accordance with the first sequence in the state as shown by FIG. 5, the engagement members 11 are disengaged from the side edge portions 8 of the front waist region 4 and thereby the front waist region 4 is disconnected from the rear waist region 6. Now the inner surfaces of the respective side edge portions 10 of the rear waist region 6 are placed again on the outer surfaces of the respective side edge portions 8 of the front waist region 4 at new positions appropriate for adjustment and the engagement members 11 are pressed against the outer surface of the front waist region 4. By pressing the engagement members 11 against the outer surface of the front waist region 4, the hooks 20 are caught by individual fibers of the nonwoven fabric layer 13 constituting the outer sheet 2 and thereby the free portions 19 of the engagement members 11 are engaged with the outer surface of the front waist region 4. In this way, the side edge portions 8 of the front waist region 4 are connected with the side edge portions 10 of the rear waist region 6 at the positions desired for fitness adjustment (See FIG. 7). In this way, parent or care personnel may connect the side edge portions 10 of the rear waist region 6 with the side edge portions 8 of the front waist region 4 at the desired positions to ensure that a dimension of the article 1A in the waist surrounding direction is adjusted in conformity with the individual wearer's waist size.

Thus the article 1A allows the fitness of the front and rear waist regions 4, 6 around the wearer's waist to be adjusted by releasing the engagement between the side edge portions 8 of the front waist region 4 and the engagement members 11 from the state of the article 1A having been once put on the wearer's body as shown by FIG. 5 and engaging again the engagement members 11 with the side edge portions 8 of the front waist region 4 at desired positions on the respective side edge portions 8. Regardless of the particular wearer's waist size, the article 1A can be appropriately tightened around the wearer's waist and such adjustment makes it possible to prevent the article 1A from slipping down during use of the article 1A.

Of the fixed portion 18 in each of the engagement members 11, the upper zone 18a and the intermediate zone 18b respectively lie on the associated ones of the transversely opposite end portions 14a, 15a of the first and second waist-surrounding elastic members 14, 15 and the lower zone 18c lies on the associated upper end portions 16a of the leg-surrounding elastic members 16 on the associated side. Such arrangement ensures that the elastic members 14, 15 are stretched in the transverse direction in operative association with the engagement members 11 and the elastic members 16 are stretched in the longitudinal direction also in operative association with the engagement members 11 as the engagement members 11 are adjustably engaged with the side edge portions 8 of the front waist region 4 at the desired positions. In this way, these elastic members 14, 15, 16 can be effectively utilized to tighten the article 1A around the wearer's waist and legs and thereby to maintain the front and rear waist regions 4, 6 in close contact with the wearer's skin.

In the article 1A, the length dimension S2 of the engagement member 11 measured in the longitudinal direction is substantially same as the length dimension S1 of the side edge portion 10 of the rear waist region 6. Such dimensioning allows each of the side edge portions 10 to be engaged over a substantially full range of the length dimension S1 with the front waist region 4. Compared to the case in which the side edge portions 10 of the rear waist region 6 are partially connected to the front waist region 4, the article 1A allows the front and rear waist regions 4, 6 to be reliably connected with each other.

Figure 9:
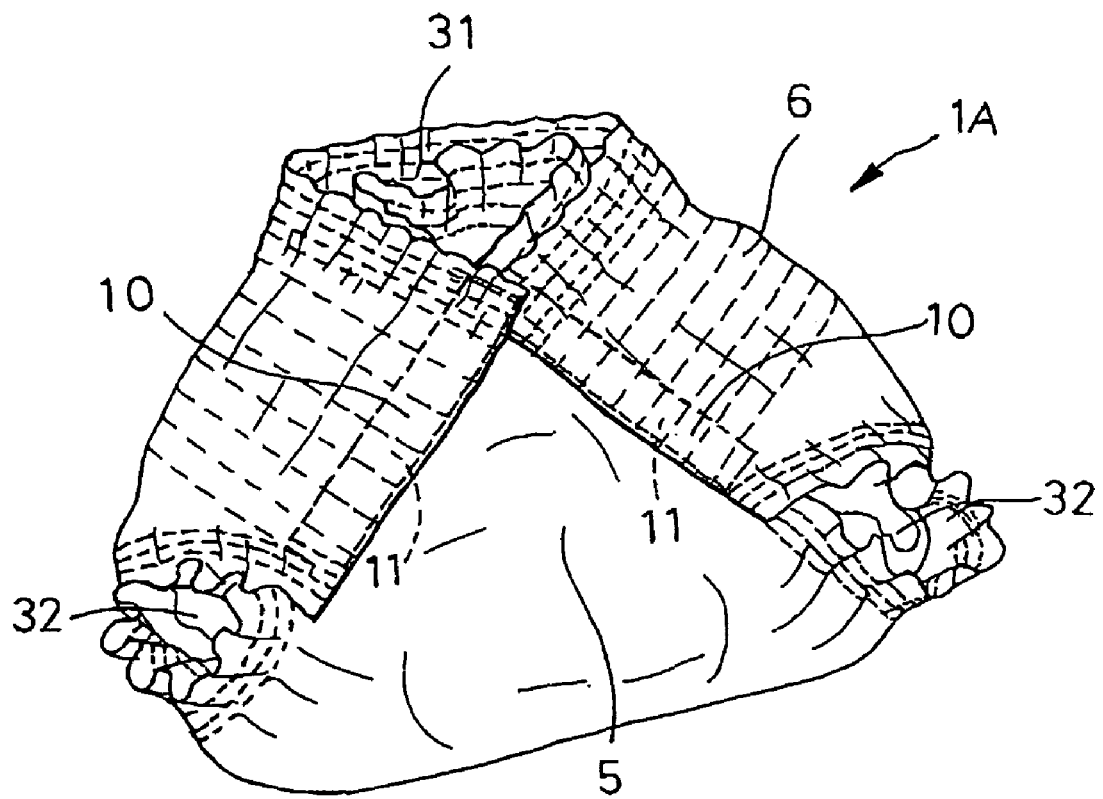
FIG. 9 is a perspective view showing the article folded for disposal.

FIG. 9 is a perspective view showing the article 1A folded ford disposal. The used article 1A maybe prepared for disposal, for example, in a manner as will be described hereunder. After the engagement members 11 have been disengaged from the front waist region 4 and the article 1A has been left off from the wearer's body, parent or care personnel may fold the crotch region 5 onto the outer surface of the front waist region 4, then draw the side edge portions 10 of the rear waist region toward a transversely intermediate zone of the crotch region 5 and press the side edge portions 10 of the rear waist region 6 against the outer surface of the crotch region 5 at desired positions. By pressing the side edge portions 10 against the crotch region 5, the hooks 20 are caught by the individual fibers of the nonwoven fabric layer 13 constituting the outer sheet 2 and thereby the free portions 19 of the respective engagement members 11 are engaged with the outer surface of the crotch region 5. The used article 1A is maintained in its folded state by the engagement members 11 and therefore ready for disposal. More specifically, the waist-hole 31 as well as the leg-holes 32 of the used article 1A are maintained in closed state and therefore it is not apprehended that body waste or odor thereof might leak out from the article 1A through the waist-hole 31 and/or the leg-holes 32.

Figure 10:
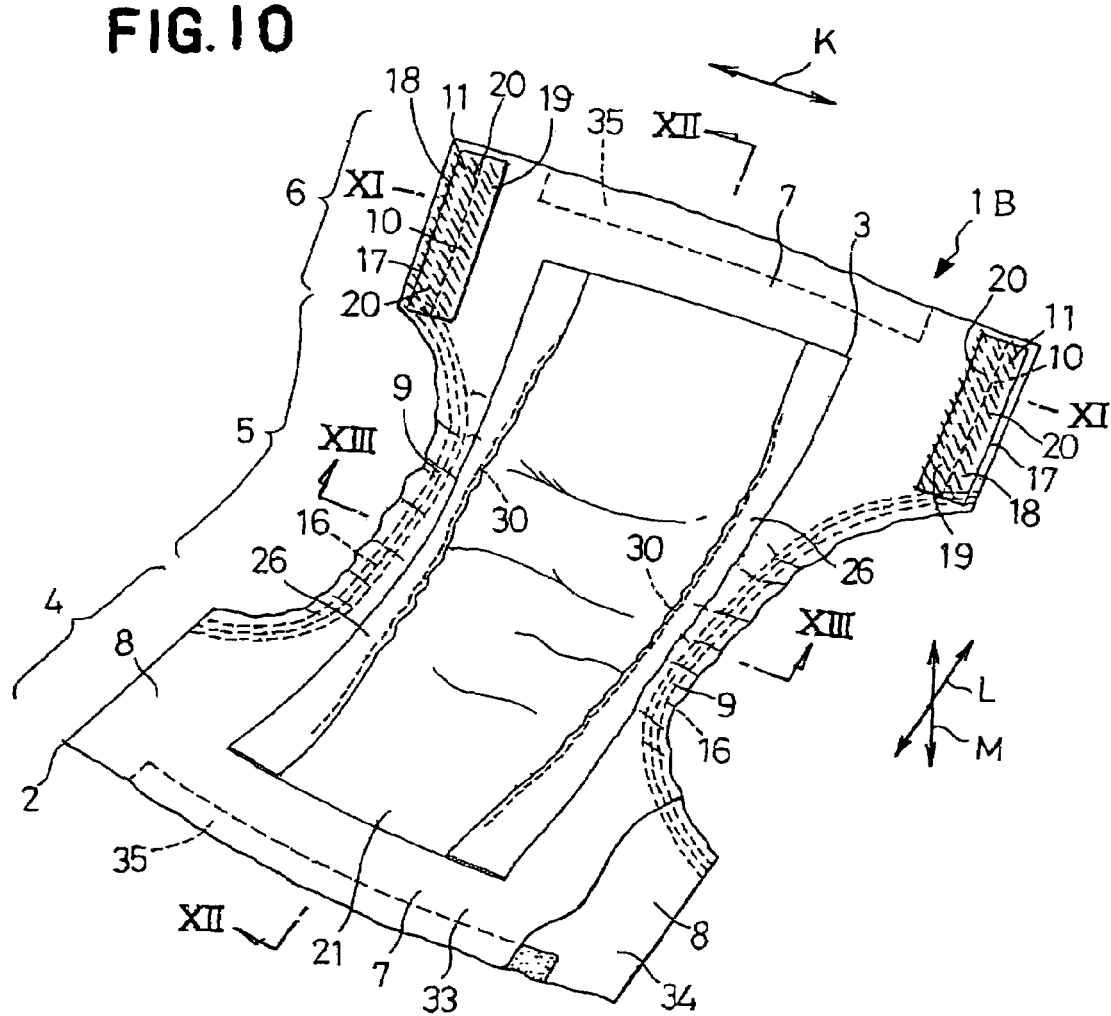
FIG. 10 is a partially cutaway perspective view showing another embodiment of the wearing article according to the invention.
Figure 11:
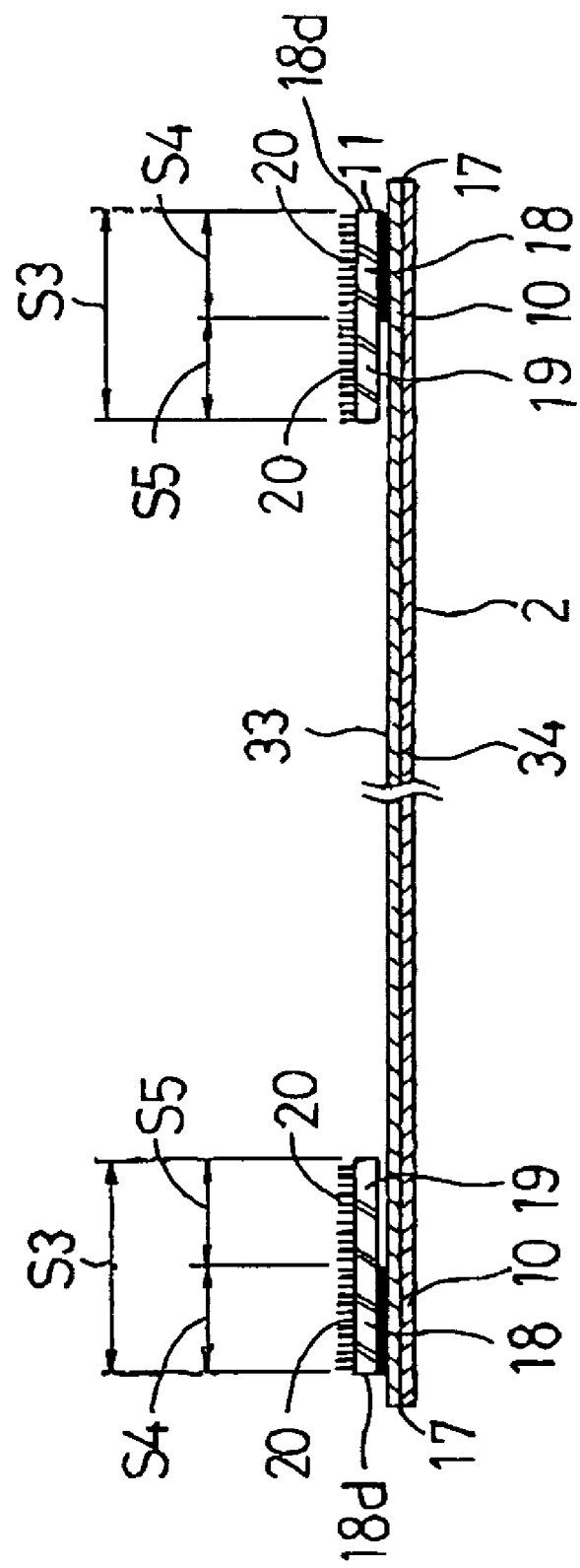
FIG. 11 is a sectional view taken along the line XI-XI in FIG. 10.
Figure 12:
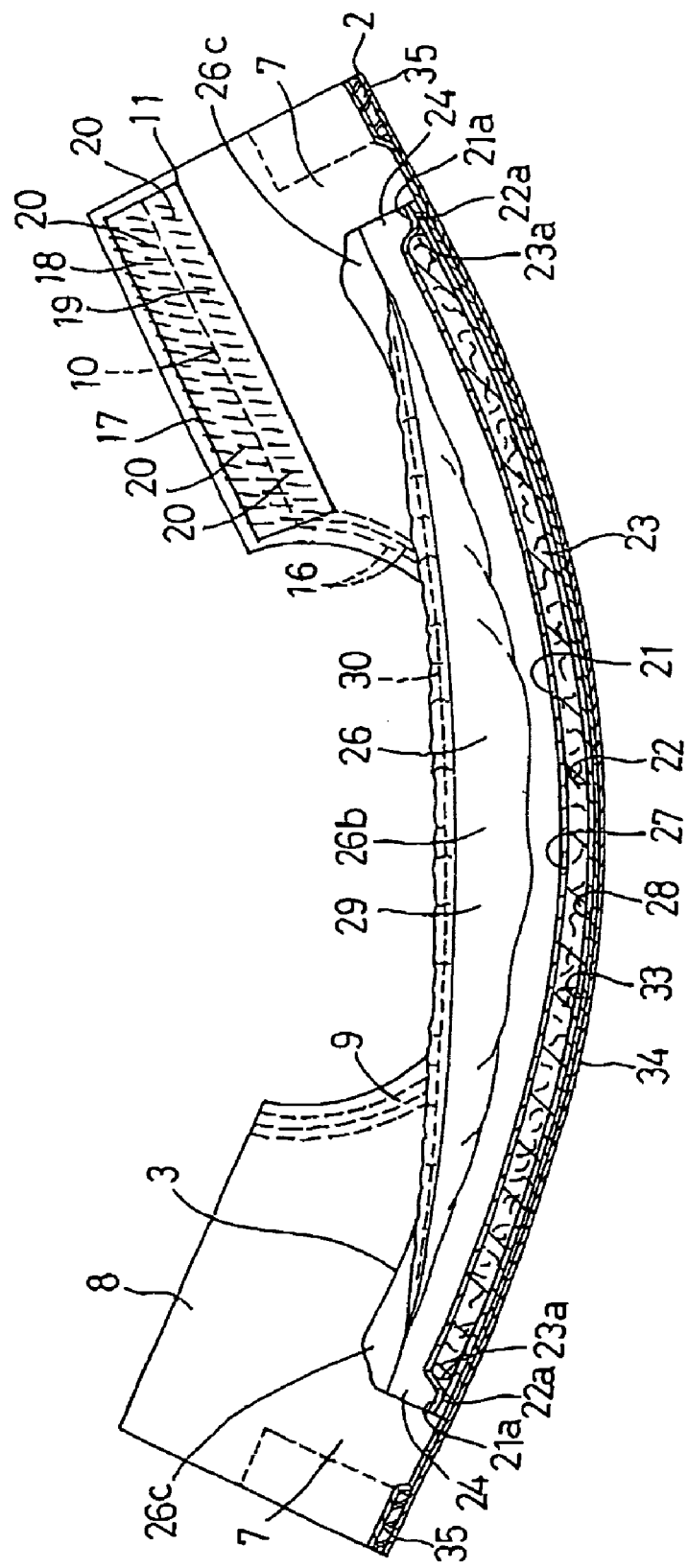
FIG. 12 is a sectional view taken along the line XII-XII in FIG. 10.
Figure 13:
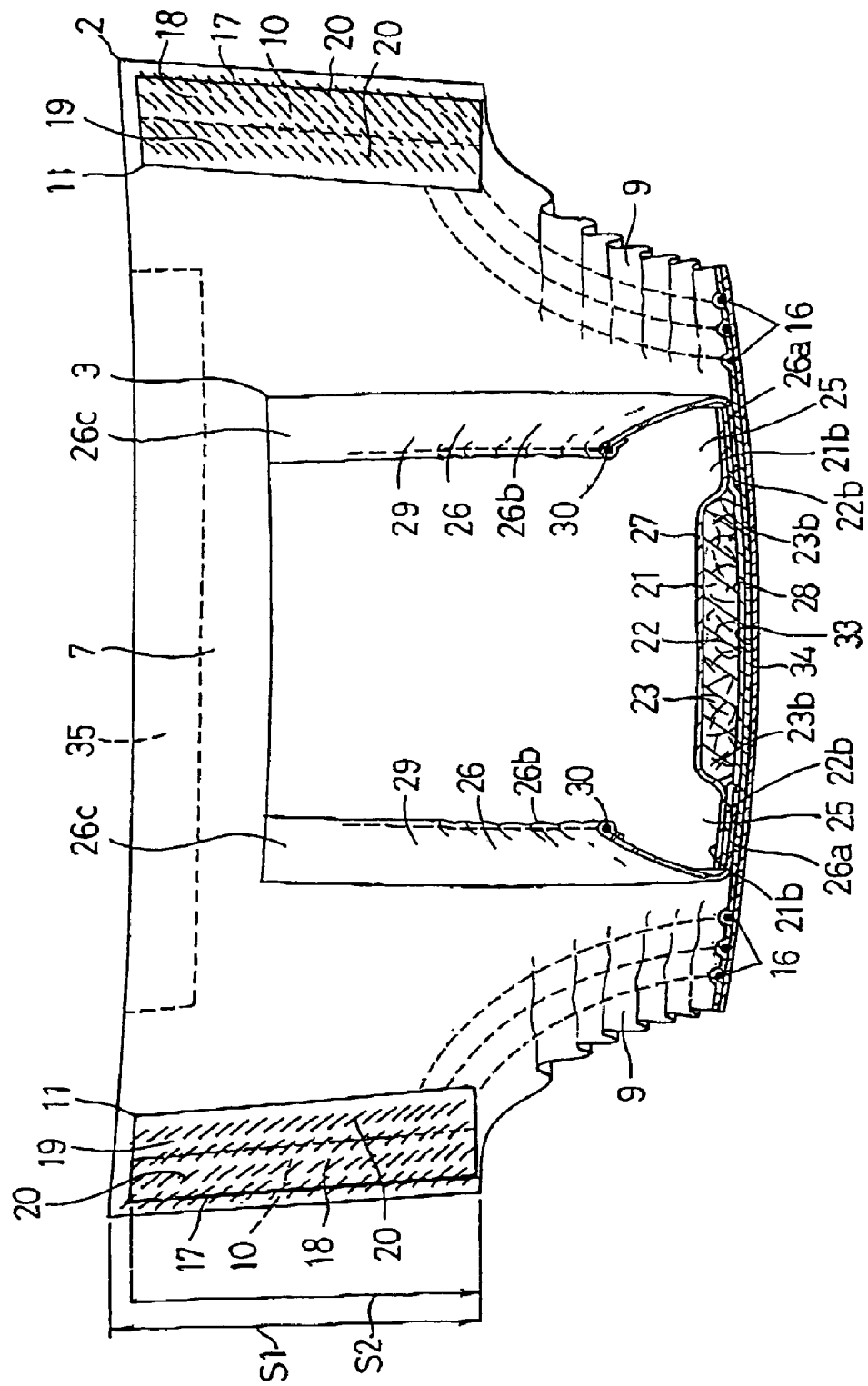
FIG. 13 is a sectional view taken along the line XIII-XIII in FIG. 10.

FIG. 10 is a perspective view showing a wearing article 1B according to another embodiment according to the invention as partially broken away, FIG. 11 is a sectional view taken along a line XI-XI in FIG. 10, FIG. 12 is a sectional view taken along a line XII-XII in FIG. 10 and FIG. 13 is a sectional view taken along a line XIII-XIII in FIG. 10. In FIG. 10, a transverse direction is indicated by an arrow K, a longitudinal direction is indicated by an arrow L and a thickness direction is indicated by an arrow M.

The article 1B comprises a liquid-impervious outer sheet 2 and a laminated panel 3 attached to the inner surface of the outer sheet 2. The article 1B defines, in a longitudinal direction, a front waist region 4, a rear waist region 6, a crotch region 5 extending between these waist regions 4, 6, longitudinally opposite end portions 7 extending in a transverse direction, and transversely opposite side edge portions 8, 9, 10 extending in a longitudinal direction. The side edge portions 8 of the front waist region 4 have a substantially same length dimension as a length dimension of the side edge portions 10 of the rear waist region 6. Engagement members 11 are attached to the side edge portions 10 of the rear waist region 6.

The outer sheet 2 defines the front and rear waist regions 4, 6, the crotch region 5, the longitudinally opposite end portions and the transversely opposite side edge portions 8, 9, 10. The outer sheet 2 is formed by composite nonwoven fabric consisting of a pair of non-stretchable hydrophobic fibrous nonwoven fabric layers 12, 13 placed upon and bonded to each other. Mutually opposed surfaces of these nonwoven fabric layers 12, 13 are intermittently bonded to each other by means of adhesive (not shown). The outer sheet 2 curves inward along the side edge portions extending in the crotch region 5 so as to describe circular arcs which are convex in the transverse direction of the article 1B. Thus, the outer sheet 2 presents a substantially hourglass-like planar shape. Waist-surrounding elastic members 35 and a plurality of leg-surrounding elastic members 16 are contractibly attached to the outer sheet 2.

The waist-surrounding elastic members 35 are belt-like members and extend along the longitudinally opposite end portions 7 in the transverse direction. The leg-surrounding elastic members 16 comprise a plurality of elastic strands extending along the side edges 8, 9, 10 in the longitudinal direction These elastic members 16, 35 are interposed between the nonwoven fabric layers 33, 34 constituting the outer sheet 2 and intermittently bonded to the mutual opposed surfaces of these nonwoven fabric layers 33, 34. Specifically, these elastic members 33, 34 are bonded to these nonwoven fabric layers 16, 35 while these elastic members 16, 35 are stretched at a predetermined ratio. The respective side edge portions 8, 10 of the front and rear waist regions 4, 6 are elastically stretchable at least in the transverse direction of the longitudinal and transverse directions because the elastic members make the outer sheet 2 elastically stretchable.

The engagement members 11 are laid on the inner surface of the rear waist region 6 along the side edge portions 10 thereof and extend in the longitudinal direction. Each of the engagement members 11 is provided in a rectangular shape which is relatively long in the longitudinal direction and its length dimension S2 measured in the longitudinal direction is substantially same as a length dimension S1 of the side edge portion 10 measured in the longitudinal direction (See FIG. 13). The engagement member 11 has a fixed portion 18 permanently bonded to the side edge portion 10 in the vicinity of its outermost edge 17 and extending in the longitudinal direction and a free portion 19 extending in parallel to and inward from the fixed portion 18 in the transverse direction of the rear waist region 6.

The fixed portion 18 has its outer surface permanently bonded to the inner surface of the outer sheet 2 (i.e., the nonwoven fabric layer 33). The free portion 19 is not permanently bonded to the outer sheet 2 and free from the outer sheet 2. The fixed portion 18 and the free portion 19 are provided on their whole inner surfaces with a plurality of hooks 20 constituting the mechanical fastener. These hooks 20 extend from the inner surfaces of these portions 18, 19 in the thickness direction of the article 1B. It should be noted here that these hooks may be replaced by adhesive of adhesive fastener known in the art.

In the engagement member 11, a length dimension S4 of the fixed portion 18 measured in the transverse direction is approximately a half of a full length dimension S3 of the engagement member 11 measured in the transverse direction and a length dimension S5 of the free portion 19 measured in the transverse direction is approximately a half of the full length dimension S3 (See FIG. 11). The outermost edge 18d of the fixed portion 18 is placed aside inward from the outermost edge 17 of the side edge portion 10.

The panel 3 comprises a liquid-pervious topsheet 21 facing the wearer's skin, a liquid-impervious backsheet 22 facing away from the wearer's skin and a liquid-absorbent core 23 interposed between these top- and backsheets 21, 22. The panel 3 serves to absorb and to retain body waste discharged by the wearer of the article 1B. The panel 3 has a substantially rectangular planar shape and extends between the front and rear waist regions 4, 6. The panel 3 has longitudinally opposite ends 24 extending in the transverse direction and transversely opposite side edges 25 extending in the longitudinal direction. In the panel 3, the outer surface of the backsheet 22 is permanently bonded to the inner surface of the outer sheet 2 (i.e., the nonwoven fabric layer 33) in intermittent or continuous manner. The transversely opposite side edges 25 of the panel 3 are respectively provided with a pair of liquid-resistant leak-barrier sheets 26 extending in the longitudinal direction. The core 23 is similar to that in the embodiment shown by FIG. 1.

The longitudinally opposite end portions 24 are formed by longitudinally opposite end portions 21a, 22a of the top- and backsheets 21, 22, respectively, extending outward in the longitudinal direction beyond the longitudinally opposite ends 23a of the core 23. In these end portions 24, the end portions 21a, 22a of the top- and backsheets 21, 22 are put flat and permanently bonded together. The transversely opposite side edge portions 25 are formed by transversely opposite side edge portions 21b, 22b of the top- and backsheets 21, 22, respectively, extending outward in the transverse direction beyond the transversely opposite side edges 23b of the core 23. In these side edge portions 25, the side edge portions 21b, 22b of the top- and backsheets 21, 22 are put flat and permanently bonded together.

The leak-barrier sheets 26 are formed by hydrophobic fibrous nonwoven fabric 29 similar to that in the embodiment shown by FIG. 1. Each of these leak-barrier sheets 26 has a fixed lateral portion 26a extending in parallel to the associated side edge 25 of the panel 3 in the longitudinal direction, a movable portion 26b extending in parallel to the fixed lateral portion 26a in the longitudinal direction, and longitudinally opposite fixed end portions 26c of the movable portion 26b. The fixed lateral portion 26a is interposed between the outer sheet 2 and the backsheet 22 and permanently bonded to the inner surface of the outer sheet 2 (i.e., the nonwoven fabric layer 33) and the outer surface of the backsheet 22. A stretchable elastic member 30 extending in the longitudinal direction is contractibly attached to the movable portion 26b in the vicinity of its upper edge. The movable portion 26b rises above the topsheet 21 and forms a barrier against body waste as the elastic member 30 contracts. The longitudinally opposite fixed end portions 26c lying on the respective end portions 25 of the panel 3 are collapsed inward as viewed in the transverse direction of the article 1B and permanently bonded in such state to the outer surface of the topsheet 21.

Figure 14:
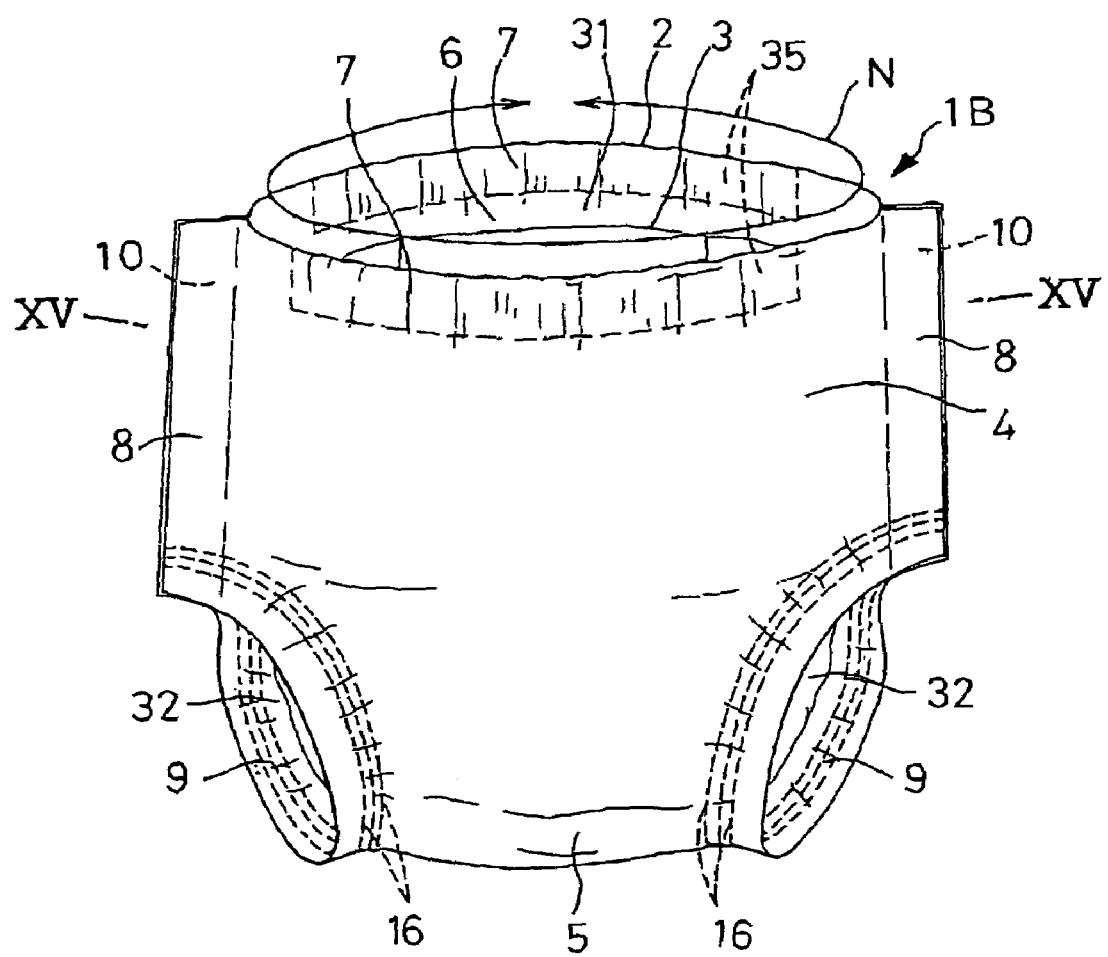
FIG. 14 is a perspective view showing the article of FIG. 10 as put on the wearer's body in one manner of wearing.
Figure 15:
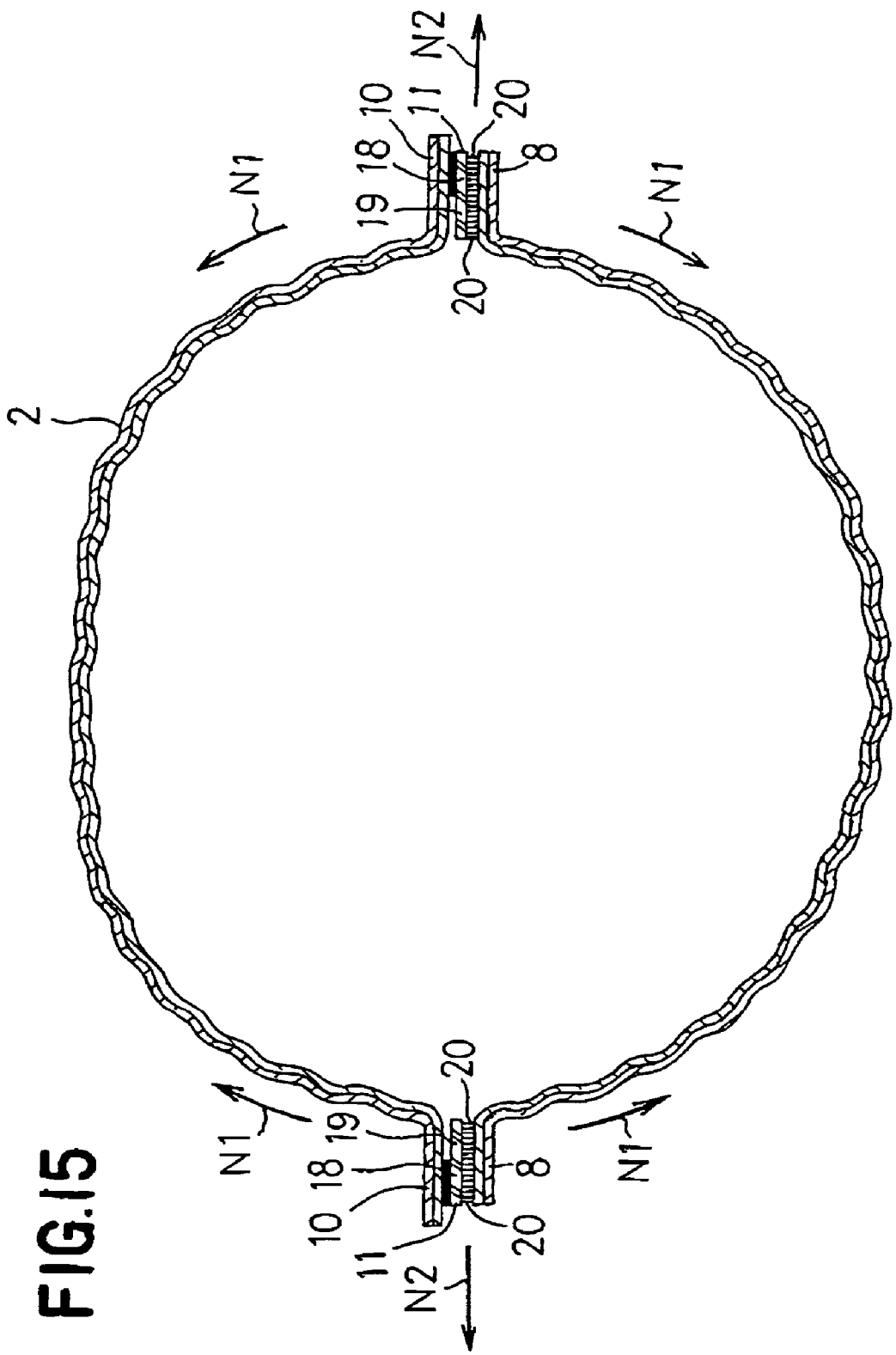
FIG. 15 is a sectional view taken along the line XV-XV in FIG. 14.
Figure 16:
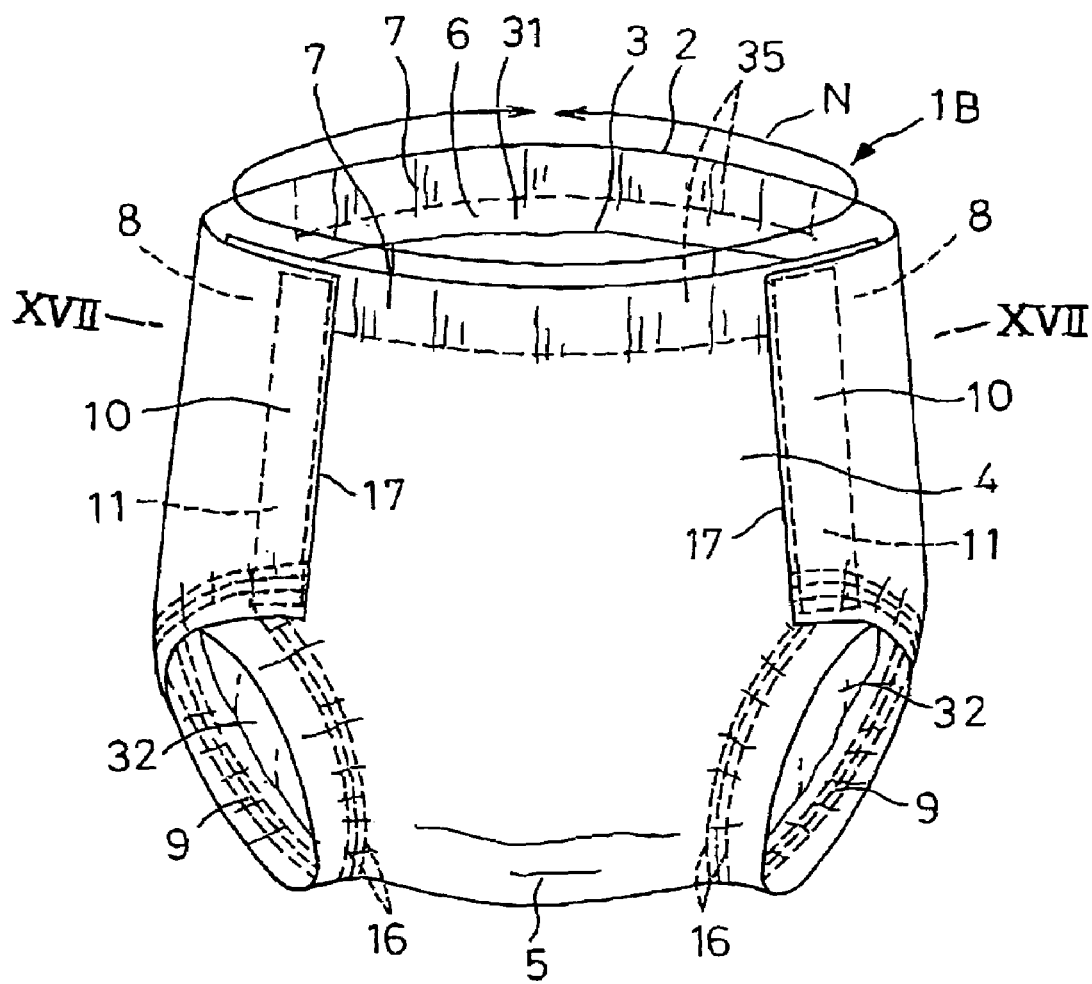
FIG. 16 is a perspective view showing the article of FIG. 10 as put on the wearer's body in another manner of wearing.
Figure 17:
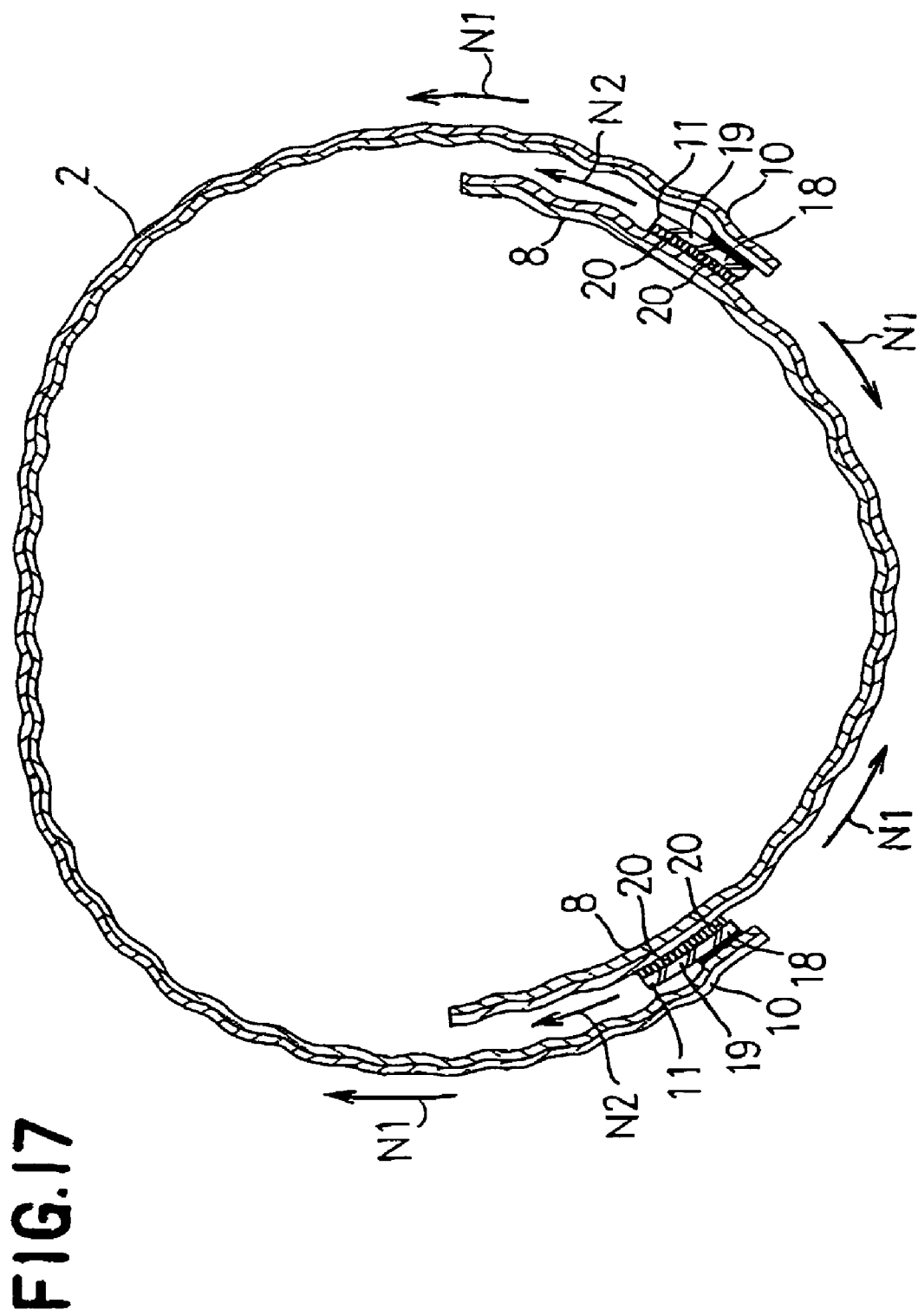
FIG. 17 is a sectional view taken along the line XVII-XVII in FIG. 16.

FIG. 14 is a perspective view showing the article 1B of FIG. 10 as put on the wearer's body in one manner of wearing, FIG. 15 is a sectional view taken along a line XV-XV in FIG. 14, FIG. 16 is a perspective view showing the article 1B of FIG. 10 as put on the wearer's body in another manner of wearing and FIG. 17 is a sectional view taken along a line XVII-XVII in FIG. 16. In FIGS. 14 and 16, a waist-surrounding direction is indicated by an arrow N. A sequence for disposal of this article 1B is same as the case of FIG. 1 and therefore its repeated description is eliminated here.

A first sequence followed by parent or care personnel to put the article 1B on the wearer's body comprises steps of placing the inner surface of the rear waist region 6 upon the inner surface of the front waist region 4 along the side edge portions 10, 8 thereof and pressing the engagement members 11 against the inner surfaces of the respective side edge portions 8 of the front waist region 4. By pressing the engagement members 11 against the inner surfaces of the side edge portions 8, the hooks 20 are caught by individual fibers of the nonwoven fabric layer 33 constituting the outer sheet 2 and thereby the fixed portion 18 and the free portions 19 of the engagement members 11 are engaged with the inner surfaces of the respective side edge portions 8 of the front waist region 4. In this way, the front and rear waist regions 4, 6 are connected with each other along the side edge portions 8, 10 thereof (See FIG. 14) whereupon the article 1B is formed with a waist-hole 31 and a pair of leg-holes 32. After the front and rear waist regions 4, 6 have been connected with each other, parent or care personnel guides the wearer's legs through the waist-hole 31, then through the leg-holes 32 and draws the article 1B upward along the wearer's waist.

Referring to FIG. 15, the side edge portions 8, 10 of the front and rear waist regions 4, 6 are pulled in the waist surrounding direction indicated by an arrow N1 as the article 1A is put on the wearer's body. Although such pulling force certainly tends to disconnect the side edge portions 8, 10 of the front and rear waist regions 4, 6 from each other, it functions not as a peeling force tending to disengage the engagement members from the side edge portions 8 of the front waist region 4 but as a shearing force indicated by an arrow N2 exerted on the side edge portions 8 of the front waist region 4 and the engagement members 11. The hooks 20 are not easily disengaged from the inner surface of the outer sheet 2 (i.e., the nonwoven fabric 33) merely by such shearing force. In this way, it is not apprehended that the front and rear waist regions 4, 6 might be unintentionally disconnected from each other during use of the article 1B.

In the article 1B put on the wearer's body in the manner as illustrated by FIG. 15, a significant shearing force is exerted primarily upon the free portions 19 of the respective engagement members 11 as the side edge portions 8, 10 of the front and rear waist regions 4, 6 are pulled in the waist surrounding direction indicated by the arrow N1. Such shearing force functions to enhance engagement between the hooks 20 formed on the free portions 19 and the individual fibers of the nonwoven fabric 33. On the contrary, a shearing force exerted upon the fixed portions 18 is not so significant as the shearing force exerted upon the free portions 19 and engagement between the hooks 20 formed on the fixed portions 18 and the individual fibers of the nonwoven fabric 33 is correspondingly moderate. In other words, the engagement between the fixed portions 18 of the respective engagement members 11 and the side edge portions a of the front waist region 4 can be easily released and thereby the side edge portions 8, 10 of the front and rear waist regions 4, 6 can be easily disconnected from one another.

A second sequence followed by parent or care personnel to put the article 1B on the wearer's body is distinguished from the first sequence as has been described above in that the second sequence includes additional steps for adjustment. If it has been found that a fitness of the front and rear waist regions 4, 6 around the wearer s waist is insufficient after the article 1B was put on the wearer's body in accordance with the first sequence in the state as shown by FIG. 14, the engagement members 11 are disengaged from the side edge portions 8 of the front waist region 4 and thereby the front waist region 4 is disconnected from the rear waist region 6. Now the inner surfaces of the respective side edge portions 10 of the rear waist region 6 are placed again on the outer surfaces of the respective side edge portions 8 of the front waist region 4 at new positions appropriate for adjustment and the engagement members 11 are pressed against the outer surface of the front waist region 4. By pressing the engagement members 11 against the outer surface of the front waist region 4, the hooks 20 are caught by individual fibers of the nonwoven fabric layer 34 constituting the outer sheet 2 and thereby the fixed portions 18 and the free portions 19 of the engagement members 11 are engaged with the outer surface of the front waist region 4. In this way, the side edge portions 8 of the front waist region 4 are connected with the side edge portions 10 of the rear waist region 6 at the positions desired for fitness adjustment (See FIG. 16). In this way, parent or care personnel may connect the side edge portions 10 of the rear waist region 6 with the side edge portions 8 of the front waist region 4 at the desired positions to ensure that a dimension of the article 1B in the waist surrounding direction is adjusted in conformity with the individual wearer's waist size.

Thus the article 1B allows the fitness of the front and rear waist regions 4, 6 around the wearer's waist to be adjusted by releasing the engagement between the side edge portions 8 of the front waist region 4 and the engagement members 11 from the state of the article 1B having been once put on the wearer's body as shown by FIG. 14 and engaging again the engagement members 11 with the side edge portions 8 of the front waist region 4 at desired positions on the respective side edge portions 8. Regardless of the particular wearer's waist size, the article 1B can be appropriately tightened around the wearer's waist and such adjustment makes it possible to prevent the article 1B from slipping down during use thereof.

Referring to FIG. 17, the side edge portions 8, 10 of the front and rear waist regions 4, 6 are pulled in the waist surrounding direction indicated by an arrow N1 as the article 1B is put on the wearer's body. Although such pulling force certainly tends to disconnect the side edge portions 8, 10 of the front and rear waist regions 4, 6 from each other, it functions not as a peeling force tending to disengage the engagement members from the side edge portions 8 of the front waist region 4 but as a shearing force indicated by an arrow N2 exerted on the side edge portions 8 of the front waist region 4 and the fixed portions 18. This is for the reason that the fixed portions 18 of the engagement members 11 are held in engagement with the side edge portions 8 by means of the hooks 20. The hooks 20 are not easily disengaged from the inner surface of the outer sheet 2 merely by such shearing force. In this way, it is not apprehended that the front and rear waist regions 4, 6 might be unintentionally disconnected from each other during use of the article 1B whether the article 1B is put on the wearer's body in the manner illustrated by FIG. 14 or in the manner illustrated by FIG. 16.

In the article 1B, the length dimension S2 of the engagement member 11 measured in the longitudinal direction is substantially same as the length dimension S1 of the side edge portion 10 of the rear waist region 6. Such dimensioning allows each of the side edge portions 10 to be engaged over a substantially full range of the length dimension S1 with the front waist region 4. The used article in may be folded in preparation for disposal by folding the crotch region 5 onto the outer surface of the front waist region 4 and engaging the fixed portions 18 and the free portions 19 of the engagement members 11 with the outer surface of the crotch region 5 similarly to the case of the article 1A shown by FIG. 1. Thus the diaper 1B is maintained in such folded state by the engagement members 11 and ready for disposal.

Figure 18:
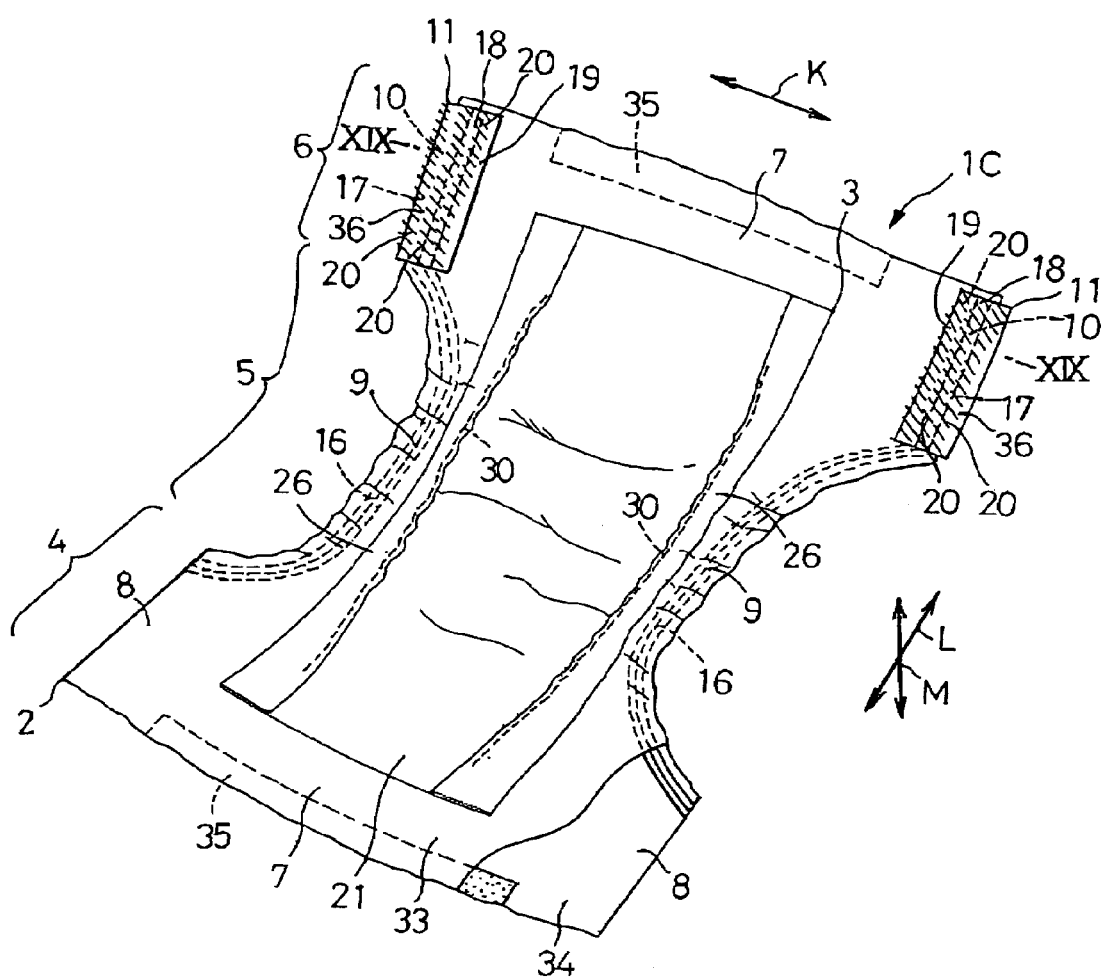
FIG. 18 is a partially cutaway perspective view showing still another embodiment of the article.
Figure 19:
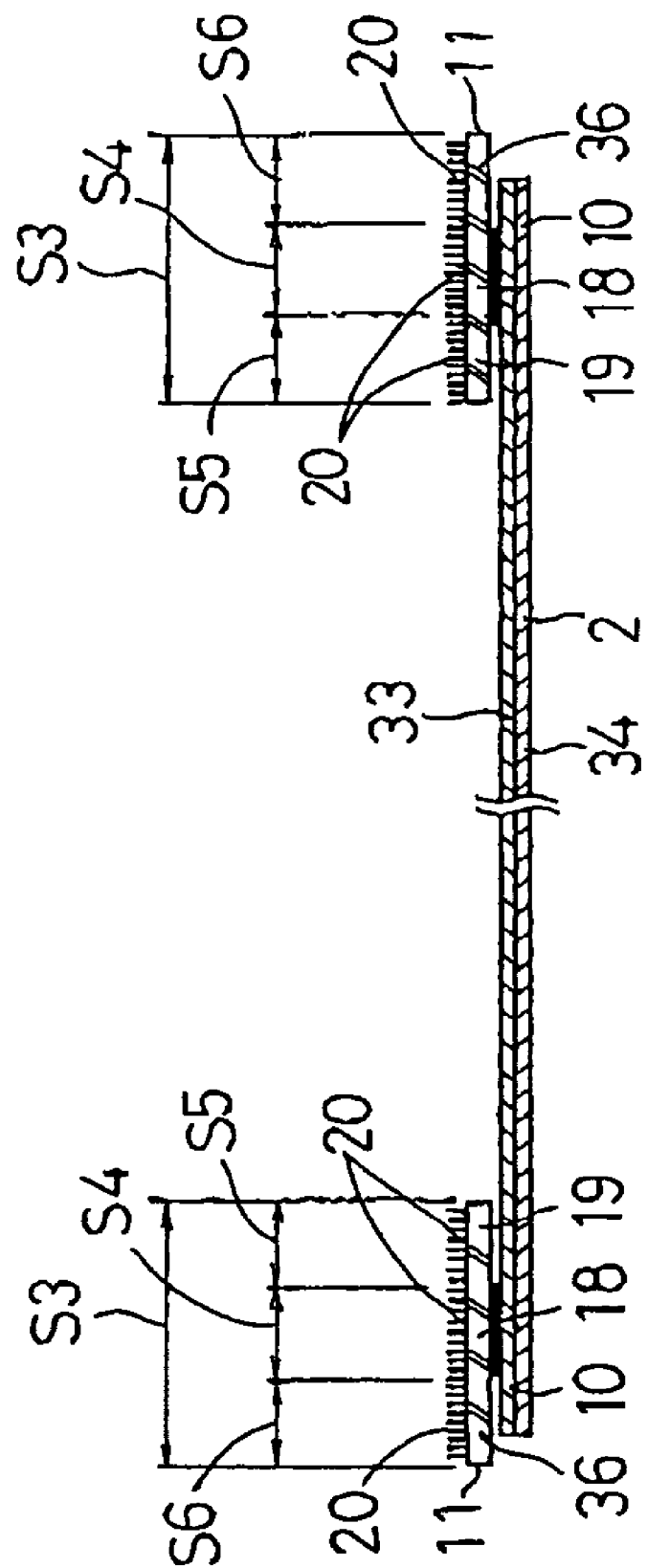
FIG. 19 is a sectional view taken along the line XI-XI in FIG. 10.

FIG. 18 is a perspective view showing an article 1C according to still another embodiment of the invention as partially broken away and FIG. 19 is a sectional view taken along a line XI-XI in FIG. 10. In FIG. 18, a transverse direction is indicated by an arrow K, a longitudinal direction is indicated by an arrow L and a thickness direction is indicated by an arrow M. While this article 1C is distinguished from the article 1B so far as the construction of the engagement members 11 is concerned, the remaining construction is common to these articles 1B and 1C. Thus similar members in these two embodiments are designated by the similar reference numerals and detailed description of these solar members is eliminated here.

The engagement members 11 are laid on the inner surface of the rear waist region 6 along the side edge portions 10 thereof and extend in the longitudinal direction. Each of the engagement members 11 is provided in a rectangular shape which is relatively long in the longitudinal direction and its length dimension measured in the longitudinal direction is substantially same as a length dimension of the side edge portion 10 measured in the longitudinal direction. The engagement member 11 has a fixed portion 18 permanently bonded to the side edge portion 10 inside its outermost edge 17 and extending in the longitudinal direction, a first free portion 19 extending in parallel to and inward from the fixed portion 18 in the transverse direction of the rear waist region 6 and a second free portion 36 extending in parallel to and outward from the fixed portion 18 in the transverse direction of the rear waist region 6.

The fixed portion 18 has its outer surface permanently bonded to the inner surface of the outer sheet 2 (i.e., the nonwoven fabric layer 33). The first and second free portions 19, 36 are not permanently bonded to the outer sheet 2. The second free portion 36 lies on the side opposed to the first free portion 19 with the fixed portion 18 therebetween and extends outward slightly beyond the outermost edge 18 of the side edge portion 10. The fixed portion 18 and the free portion 19 as well as the first and second free portions 19, 36 are provided on their whole inner surfaces with a plurality of hooks 20 constituting the mechanical fastener. These hooks 20 extend from the inner surfaces of these portions 18, 19, 36 in the thickness direction of the article 1B. It should be noted here that the hooks 20 may be replaced by adhesive of the adhesive fastener known in the art. A length dimension S4 of the fixed portion 18 is approximately ⅓ of the full length dimension S3 of the engagement member 11 and length dimensions S5, S6 of the first and second free portions 19, 36, respectively, correspond to approximately ⅓ of the full length dimension S3 of the engagement member 11.

Figure 20:
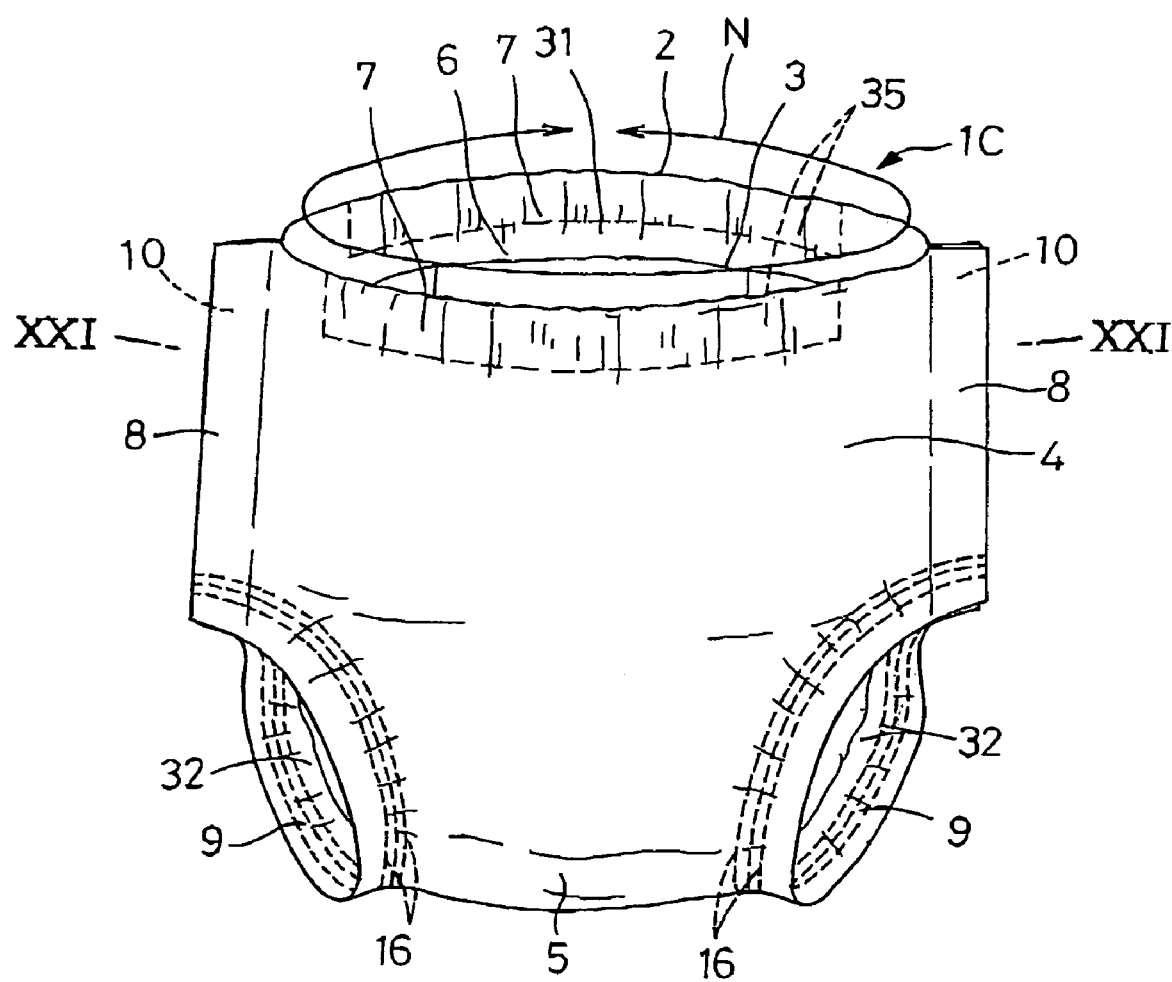
FIG. 20 is a perspective view showing the article of FIG. 18 as put on the wearer's body in one manner of wearing.
Figure 21:
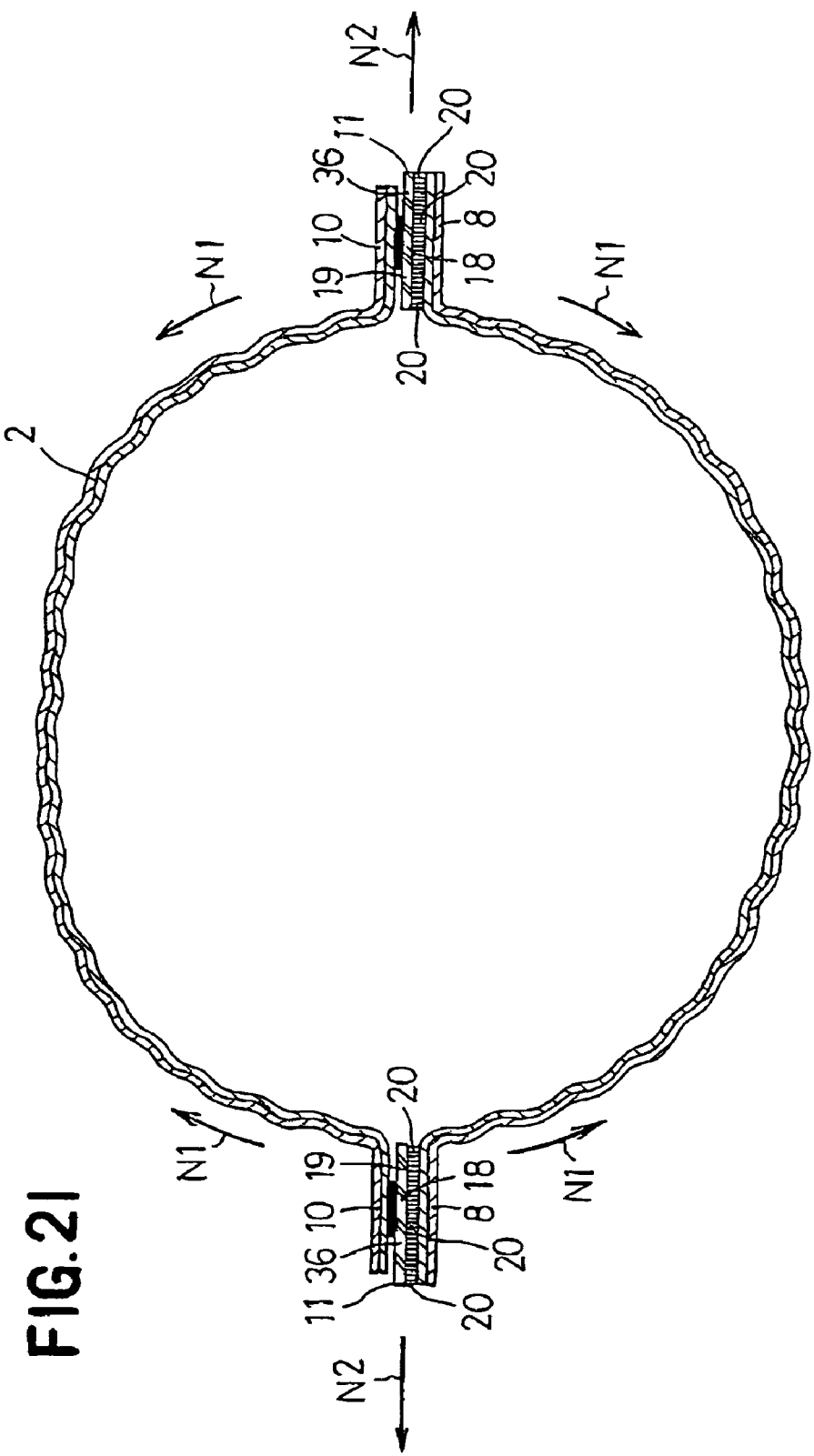
FIG. 21 is a sectional view taken along the line XXI-XXI in FIG. 20.
Figure 22:
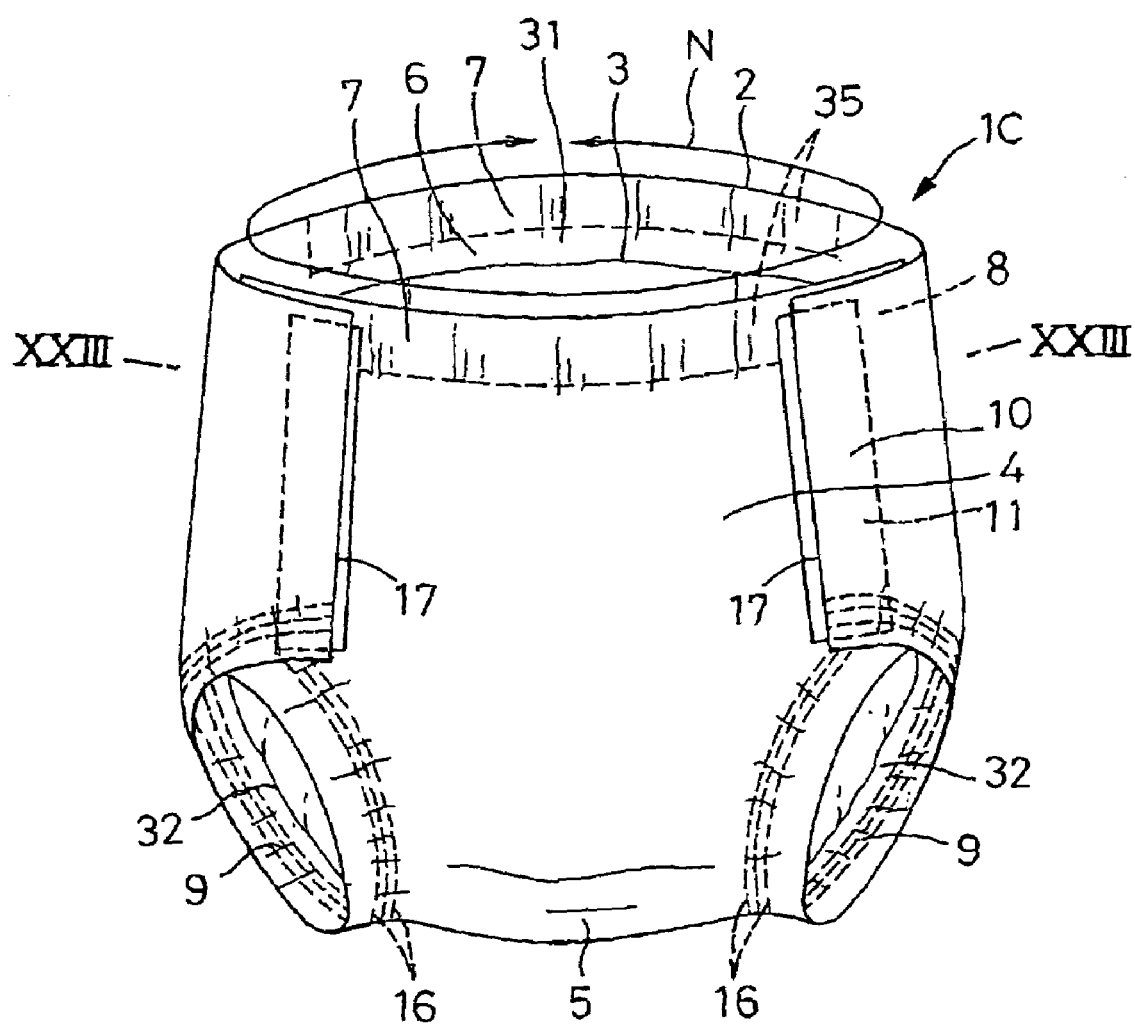
FIG. 22 is a perspective view showing the article of FIG. 18 as put on the wearer's body in another manner of wearing.
Figure 23:
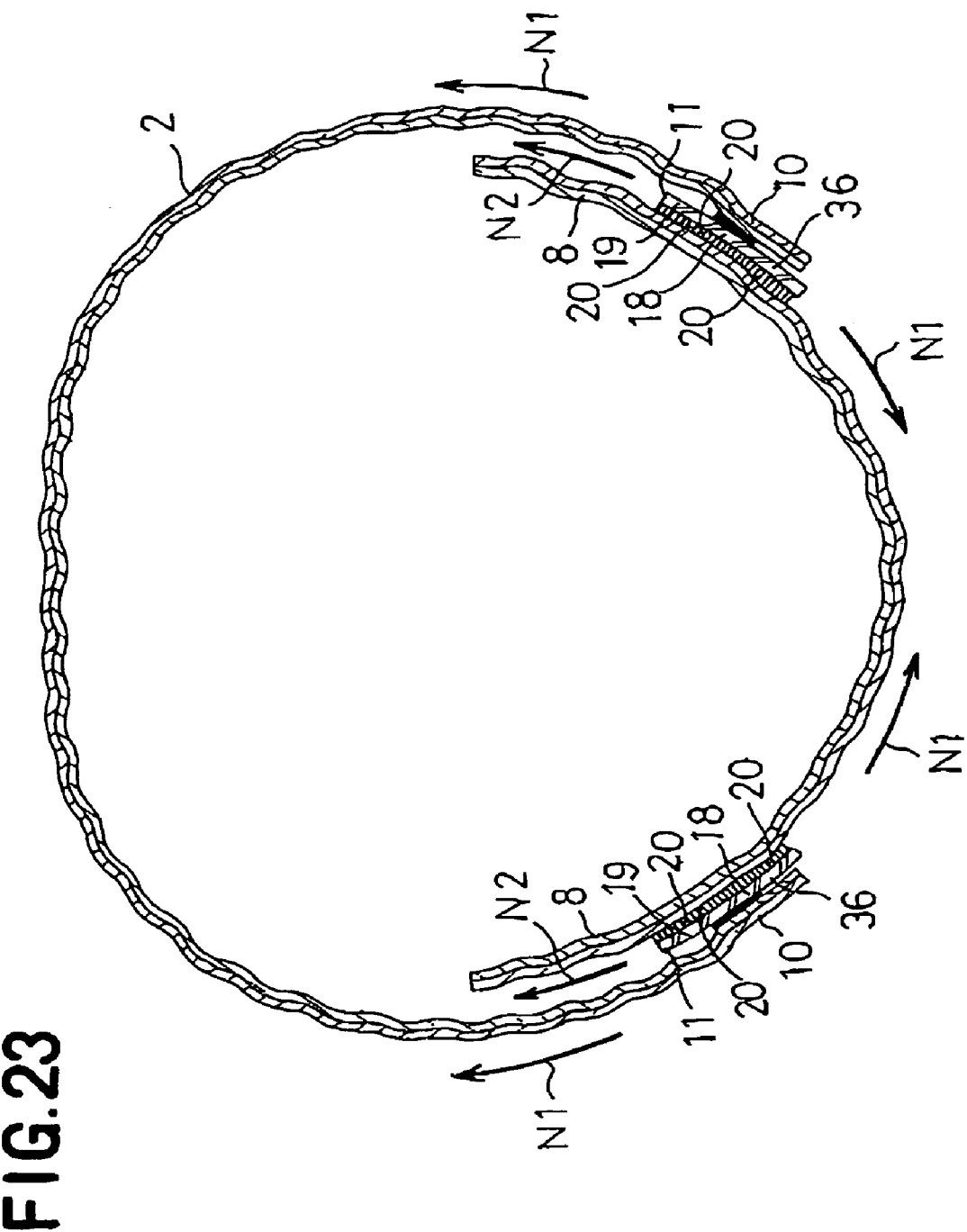
FIG. 23 is a sectional view taken along the line XXIII-XXIII in FIG. 22.

FIG. 20 is a perspective view showing the article 1C of FIG. 18 as put on the wearer's body in one manner of wearing, FIG. 21 is a sectional view taken along a line XXI-XXI in FIG. 20, FIG. 22 is a perspective view showing the article 1C of FIG. 18 as put on the wearer's body in another manner of wearing and FIG. 23 is a sectional view taken along a line XXIII-XXIII in FIG. 22. In FIGS. 20 and 22, a waist-surrounding direction is indicated by an arrow L1. A sequence for wearing as well as disposal of this article 1C is same as those in the cases of FIGS. 1 and 10 and a repeated description thereof is eliminated here.

In the article 1C, the fixed portions 18 as well as the first and second free portions 19, 26 of the respective engagement members 11 are adapted to be engaged with the inner surfaces of the respective side edge portions of the front waist region 4 and thereby to connect the side edge portions 8, 10 of the front and rear waist regions 4, 6, respectively, with one another (See FIG. 20). Referring to FIG. 21, the side edge portions 8, 10 of the front and rear waist regions 4, 6 are pulled in the waist surrounding direction indicated by an arrow N1 as the article 1C is put on the wearer's body. Although such pulling force certainly tends to disconnect the side edge portions 8, 10 of the front and rear waist regions 4, 6 from each other, it rather functions as a shearing force indicated by an arrow N2 exerted on the side edge portions 8 of the front waist region 4 and the engagement members 11. Therefore, the hooks 20 are not easily disengaged from the inner surface of the outer sheet 2 and it is not apprehended that the front and rear waist regions 4, 6 might be unintentionally disconnected from each other during use of the article 1C shown by Fog. 20.

In the article 1C, the fixed portions 18 as well as the first and second free portions 19, 26 of the respective engagement members 11 are adapted to be engaged with the inner surfaces of the respective side edge portions of the front waist region 4 so that the outer surface of the side edge portions 8 of the front waist region 4 maybe engaged, at desired positions thereof, with the side edge portions 10 of the rear waist region 6 (See FIG. 22). Even when the side edge portions 8, 10 of the front and rear waist regions 4, 6 are pulled in the waist surrounding direction indicated by the arrow N1 and such pulling force tends to disconnect the side edge portions 8, 10 of the front and rear waist regions 4, 6 from one another, engagement of the fixed portions 18 and the second free portions 36 with the outer surface of the side edge portions 8 of the front waist region 4 prevents such pulling force from functioning as a peeling force exerted on these portions 18, 36, 8. Namely, such pulling force rather functions as a shearing force exerted on these portions 18, 36, 8 as indicated by the arrow N2 in FIG. 23. The hooks 20 are not easily disengaged from the inner surface of the outer sheet 2 merely by such shearing force and it is not apprehended that the front and rear waist regions 4, 6 might be unintentionally disconnected from each other during use of the article 1C. Even if a peeling force tends to affect the fixed portions 18, such peeling force is effectively restricted by engagement of the second free portions 36 of the respective engagement members 11 with the outer surface of the side edge portions 8 by means of the hooks 20.

In the article 1C, the first and second free portions 19, 36 of the engagement members 11 are engaged with the outer surface of the side edge portions 8 by means of the hooks so as to enhance engagement between the front waist region 4 and the engagement members 11. In this way, it is possible to maintain the engagement members 11 and the side edge portions 8 in these free portions 19, 36 even if any peeling force is exerted on the fixed portions 18.

The article 1C allows a fitness of the article 1C around the wearer's waist to be adjusted by engaging again the engagement members 11 with the side edge portions 8 of the front waist region 4 at desired positions on the side edge portions 8. The article 1C further allows the side edge portions 10 of the rear waist region 6 to be engaged with the front waist region 4 substantially over the full length dimension of the side edge portions 10 by means of the engagement members 11 and thereby allows the front and rear waist regions 4, 6 to be reliably connected with each other.

The used article 1C may be folded in the same manner as in the case of the article 1A of FIG. 1 for disposal thereof. Specifically, the crotch region 5 may be folded onto the outer surface of the front waist region 4 and then the fixed portions 18 and the first and second free portions 19, 36 may be engaged with the outer surface of the crotch region. The used article 1C is maintained in such folded state and ready for disposal.

Material for the topsheet 21 is not limited to the hydrophilic fibrous nonwoven fabric and it is possible to form the topsheet 21 by hydrophobic fibrous nonwoven fabric having a plurality of apertures. It is possible to use breathable liquid-impervious plastic film as material for the backsheet 22. The outer sheet 2, the backsheet 22 and the leak-barrier sheets 26 may be formed also by composite nonwoven fabric (SM nonwoven fabric or SMS nonwoven fabric) consisting of melt blown fibrous nonwoven fabric having a high water-resistance and spun bond fibrous nonwoven fabric being high in strength as well as in flexibility laminated on at least one side of the melt blown fibrous nonwoven fabric.

Materials for the fibrous nonwoven fabric layers may be selected from a group consisting of spun lace-, needle punch-, melt blown-, thermal bond-, spun bond- and chemical bond-nonwoven fabric layers. Material for the hydrophilic fibrous nonwoven fabric may be selected from a group consisting of synthetic fiber modified to be hydrophilic, semi-synthetic fiber, regenerated fiber and mixture thereof. The hydrophobic fibrous nonwoven fabric may contain water-repellent finished semi-synthetic fiber or regenerated fiber. Although not specified, the synthetic fiber may be selected from a group consisting of polyester-, polyacrylonitril-, polyvinyl chloride-, polyethylene-, polypropylene- and polystyrene-based synthetic fibers. It is also possible to use the synthetic fiber selected from a group consisting of core-sheath conjugate fiber, side-by-side conjugate fiber, modified macaroni fiber, microporous fiber and fused type conjugate fiber.

The stretchable fibrous nonwoven fabric layers 33, 34 constituting the outer sheet 2 of FIGS. 10 and 18 may be formed by melt blown nonwoven fabric or spun bond nonwoven fabric. It is possible to use, as component fiber of the stretchable nonwoven fabric layers 33, 34, stretchable fiber melt spun from thermoplastic elastomer resin. It is also possible to form the outer sheet 2 by composite nonwoven fabric consisting of stretchable hydrophobic fibrous nonwoven fabric made of thermoplastic elastomer resin fiber and hydrophobic fibrous nonwoven fabric made of crimped fiber melt spun from thermoplastic synthetic resin selected from a group consisting of polypropylene, polyethylene and polyester laminated on at least one surface of the aforementioned hydrophobic fibrous nonwoven fabric.

Permanently bonding of the sheets 2, 21, 22, 26 to one another, permanently bonding of the core 23 to the sheets 21, 22 and permanently bonding of the elastic members 30 to the sheet 26 may be achieved by use of adhesive. It is preferred to coat the outer sheet 2, the top- and backsheets 21, 22 and the leak-barrier sheets 26 with the adhesive in a pattern selected from a group consisting of spiral pattern, wave-pattern, zig-zag pattern, dotted pattern and stripe-pattern. By coating the top- and backsheets 21, 22 and the leak-barrier sheets 26 with the adhesive in such pattern, these sheets 2, 21, 22, 26 can be intermittently and permanently bonded one to another, the core 23 can be intermittently and permanently bonded to the sheets 21, 22 and the elastic members 30 can be intermittently and permanently bonded to the sheet 26. The outer sheet 2 may be permanently bonded to the fixed portions 18 of the respective engagement members 11 by use of adhesive or welding technique such as sonic sealing or heat sealing. The adhesive may be selected from a group consisting of hot melt adhesive, acrylic adhesive and rubber adhesive.

When the engagement members 11 are permanently bonded to the outer sheet 2 using adhesive, a content of finish surface active agent in the nonwoven fabric layers 12, 13, 33, 34 constituting the outer sheet 2 is preferably 0.04 wt per total weight of these nonwoven fabric layers as measured by solvent extraction method (prescribed by JIS L 1015 7.22). If the content of the finish surface active agent exceeds 0.04 wt. the finish surface active agent will progressively deteriorate an adhesive force of the adhesive as the time elapses and an adhesive strength between the fixed portions 18 and the outer sheet 2 will be correspondingly deteriorated until the fixed portions 18 may be peeled off from the outer sheet 2. So far as the content of the finish surface active agent is less than 0.04 wt, the adhesive is reliably protected against deterioration of its adhesive force and, even if the articles 1A, 1B, 1C are stored for long period, the adhesive strength between the fixed portions 18 of the engagement members 11 and the outer sheet 2 is protected from deterioration. The finish surface active agent may be selected from a group consisting of anionic, nonionic, cationic, amphoteric surface active agents and mixtures thereof. Anionic or nonionic surface active agent may contain, if necessary to enhance adherence to the fiber, fatty wax, fatty acid, higher alcohol, mineral oil or hardened oil.

While the articles 1A, 1B, 1C have been illustrated and described to have the engagement members 11 attached to the inner surface of the side edges 10 of the rear waist region 6, it is also possible to attach the engagement members to the inner surface of the side edge portions 8 of the front waist region 4.

What is claimed is:

1. A disposable wearing article, comprising:
   front and rear waist regions each having opposite inner and outer surfaces;
   a crotch region extending in a longitudinal direction of said article between said front and rear waist regions; and
   a pair of engagement members respectively joined to the inner surface of one of said waist regions in transversely opposite side edge portions of said one of said waist regions;
   wherein each of said engagement members has opposite inner and outer surfaces, the outer surface of said engagement member faces the inner surface of said one of said waist regions, and the inner surface of said engagement member faces away from the inner surface of said one of said waist regions;
   wherein each of said engagement members comprises:
   a fixed portion in which the outer surface of said engagement member is permanently directly attached to the inner surface of the respective side edge portion of said one of said waist regions;
   a free portion free of direct attachment to the respective side edge portion of said one of said waist regions, and extending continuously from the fixed portion exclusively inwardly toward the other engagement member in a transverse direction of said article, wherein the outer surface of said engagement member in the free portion is spaced from the inner surface of the respective side edge portion of said one of said waist regions by an air gap; and
   a fastening element disposed on the inner surface of said engagement member in said free portion and releasably engageable with the inner or outer surface of the other one of said waist regions for coupling said waist regions together to form a waist hole in use;
   wherein a width measured in the transverse direction of said fixed portion is about the same as that of the free portion and about half of that of the entire engagement member.

2. The article according to claim 1, wherein
   the entire inner surface of each of said engagement member in the fixed portion is free of any fastening elements that are releasably engageable with any of the outer and inner surfaces of the other waist region; and
   the entire outer surface of each of said engagement member is permanently directly attached to the inner surface of the respective side edge portion of said one of said waist regions.

3. The article according to claim 1, wherein the fastening element is releasably engageable with both the inner and outer surfaces of the other one of said waist regions.

4. A disposable wearing article, comprising:
   front and rear waist regions each having opposite inner and outer surfaces;
   a crotch region extending in a longitudinal direction of said article between said waist regions; and
   a pair of engagement members respectively joined to the inner surface of one of said waist regions in transversely opposite side edge portions of said one of said waist regions;
   wherein each of said engagement members has opposite inner and outer surfaces, the outer surface of said engagement member faces the inner surface of said one of said waist regions, and the inner surface of said engagement member faces away from the inner surface of said one of said waist regions;
   wherein each of said engagement members comprises:
   a fixed portion, wherein the entire outer surface of said engagement member in said fixed portion is permanently directly attached to the inner surface of the respective side edge portion of said one of said waist regions;
   a free portion free of direct attachment to the respective side edge portion of said one of said waist regions, and extending, in cantilever fashion, continuously from the fixed portion exclusively inwardly toward the other engagement member in a transverse direction of said article, wherein the outer surface of said engagement member in the free portion is spaced from the inner surface of the respective side edge portion of said one of said waist regions; and
   a fastening element disposed on the inner surface of said engagement member in said free portion and releasably engageable with the inner or outer surface of the other one of said waist regions for coupling said waist regions together to form a waist hole and a pair of leg holes in use;
   wherein a width measured in the transverse direction of said fixed portion is about half of that of the entire engagement member.

5. The article according to claim 4, wherein
   said fastening element comprises either hooks of a mechanical fastener or adhesive of an adhesive fastener; and
   said hooks or adhesive occupy or occupies substantially an entirety of the inner surface of the free portion of said engagement member.

6. The article according to claim 4, wherein said fastening element comprises hooks distributed over substantially the entire length and width of the inner surface of said free portion, and wherein the entire inner surface of the respective fixed portion is free of hooks, loops and adhesive.

7. The article according to claim 1, wherein
   said fastening element comprises either hooks of a mechanical fastener or adhesive of an adhesive fastener; and
   said hooks or adhesive occupy or occupies substantially an entirety of the inner surface of the free portion of said engagement member.

8. The article according to claim 1, wherein said fastening element comprises hooks distributed over substantially the entire length and width of the inner surface of said free portion, and wherein the entire inner surface of the respective fixed portion is free of any fastening elements that are releasably engageable with any of the outer and inner surfaces of the other waist region.

9. The article according to claim 8, wherein
the hooks are releasably engageable with both the inner and outer surfaces of the other one of said waist regions; and
when the hooks of the engagement members are releasably engaged with the inner surface of the other one of said waist regions to couple said waist regions together to form the waist hole and leg holes,
the side edge portions of said waist regions are bent outwardly in a radial direction of the waist hole to have their inner surfaces facing each other, and
each of the engagement members is entirely positioned between the inner surfaces of the outwardly bent respective side edge portions of said waist regions.

10. The article according to claim 9, wherein
when the hooks of the engagement members are releasably engaged with the inner surface of the other one of said waist regions to couple said waist regions together to form the waist hole and leg holes,
the free portion of each of said engagement members is entirely located inward, in the transverse direction, of the respective fixed portion which is free of direct attachment to the other wait region and defines a gripping portion for a user to hold and pull the engagement member off the other waist region after use or when adjustment to the waist hole is to be made.

11. The article according to claim 5, wherein the entire inner surface of each said fixed portion is free of any fastening elements that are releasably engageable with any of the outer and inner surfaces of the other waist region.

12. The article according to claim 11, wherein
said fastening elements are releasably engageable with both the inner and outer surfaces of the other one of said waist regions; and
when the fastening elements of the engagement members are releasably engaged with the inner surface of the other one of said waist regions to couple said waist regions together to form the waist hole and leg holes,
the side edge portions of said waist regions are bent outwardly in a radial direction of the waist hole to have their inner surfaces facing each other, and
each of the engagement members is entirely positioned between the inner surfaces of the outwardly bent respective side edge portions of said waist regions.

13. The article according to claim 12, wherein
when the fastening elements of the engagement members are releasably engaged with the inner surface of the other one of said waist regions to couple said waist regions together to form the waist hole and leg holes,
the free portion of each of said engagement members is entirely located inward, in the transverse direction, of the respective fixed portion which is free of direct attachment to the other wait region and defines a gripping portion for a user to hold and pull the engagement member off the other waist region after use or when adjustment to the waist hole is to be made.

* * * * *

UNITED STATES PATENT AND TRADEMARK OFFICE
CERTIFICATE OF CORRECTION

PATENT NO. : 7,547,299 B2
APPLICATION NO. : 10/920310
DATED : June 16, 2009
INVENTOR(S) : Toshifumi Otsubo et al.

It is certified that error appears in the above-identified patent and that said Letters Patent is hereby corrected as shown below:

On the title page, the names of the inventors should read as follows:

Item (75) Inventors: Toshifumi OTSUBO, Kagawa-ken (JP); Tomoko SUGITO, Kagawa-ken (JP)

Signed and Sealed this

Twenty-fifth Day of August, 2009

David J. Kappos
*Director of the United States Patent and Trademark Office*